United States Patent [19]

Rennex

[11] Patent Number: 4,967,734

[45] Date of Patent: Nov. 6, 1990

[54] ENERGY-EFFICIENT RUNNING BRACE

[76] Inventor: Brian G. Rennex, 2232 Antiqua Ct., Reston, Va. 22091

[21] Appl. No.: 246,279

[22] Filed: Sep. 19, 1988

Related U.S. Application Data

[62] Division of Ser. No. 91,130, Aug. 31, 1987, abandoned.

[51] Int. Cl.$^5$ ............................................. A61F 5/00
[52] U.S. Cl. .................................. 128/80 G; 272/70; 272/114
[58] Field of Search ............... 128/80 G, 80 R, 382; 272/114, 70, 70.1, 70.3, 70.4, 110, 115, 135, DIG. 9

[56] References Cited

U.S. PATENT DOCUMENTS

| | | | |
|---|---|---|---|
| 1,575,847 | 3/1926 | King et al. | 272/114 X |
| 3,074,715 | 1/1963 | Taylor | 272/114 |
| 3,181,862 | 5/1965 | White | 272/114 |
| 3,765,693 | 10/1973 | Morrison et al. | 272/114 X |
| 4,243,218 | 1/1981 | DeSousa | 272/114 |
| 4,438,919 | 3/1984 | Gamzo | 272/114 X |
| 4,557,257 | 12/1985 | Fernandez et al. | 128/80 G |
| 4,872,665 | 10/1989 | Chareire | 272/70 |

FOREIGN PATENT DOCUMENTS

| | | | |
|---|---|---|---|
| 1253655 | 8/1986 | U.S.S.R. | 272/114 |
| 2156476 | 10/1985 | United Kingdom | 272/114 |

*Primary Examiner*—Edgar S. Burr
*Assistant Examiner*—Moshe I. Cohen
*Attorney, Agent, or Firm*—Lowe, Price, LeBlanc Becker & Shur

[57] ABSTRACT

This invention relates to a resilient leg brace which acts in parallel with a runner's legs to support the weight during foot impact, to store the kinetic energy of vertical motion, and to release said energy thrusting the runner back into the air during take-off. The running brace is energy efficient in that it stores and releases the maximum amount of said energy, which means that the leg muscles do not need to supply as much energy to lift the runner's weight during each step. Also, the running brace protects the legs and other parts of the body from damage due to impact. The leg brace is attached to a pelvic harness, and optional back and neck braces are attached to the shoulders and the chin for the protection of the back and neck from impact shock. The improvements include means to put energy into the energy storage means using the legs while airborne or the arms at any time, means to achieve an asymmetric brace travel using sequential springs, means to achieve a constant force curve using pairs of springs, means to support a neck and a back brace on top of the running brace, and means for an energy storage mechanism which works in a manner similar to a leg muscle.

5 Claims, 14 Drawing Sheets

FIG. 5
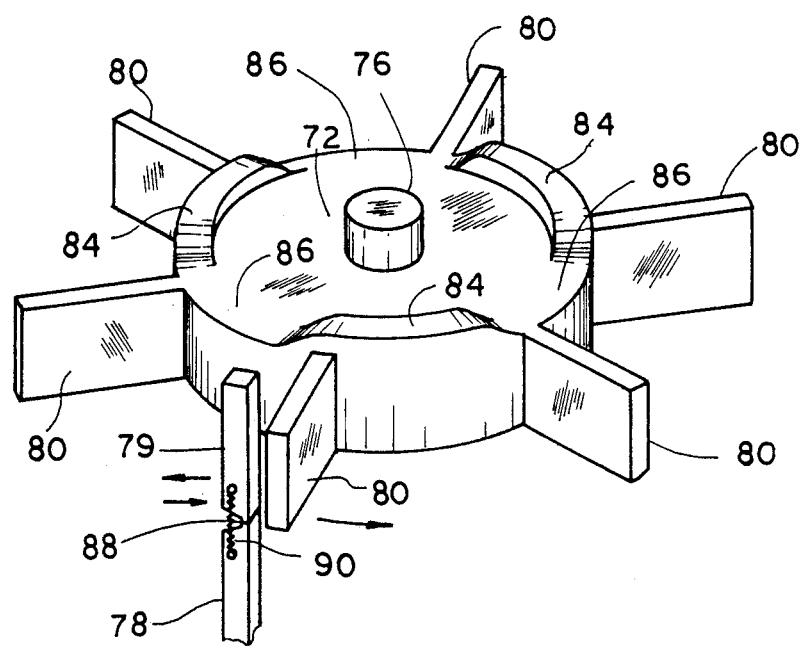
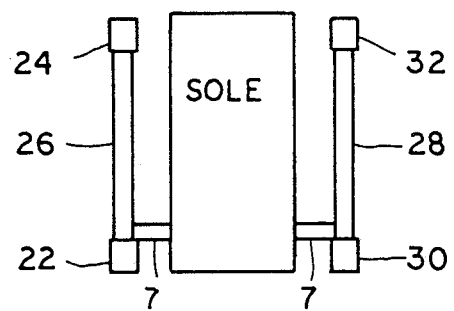
FIG. 6

FIG.12
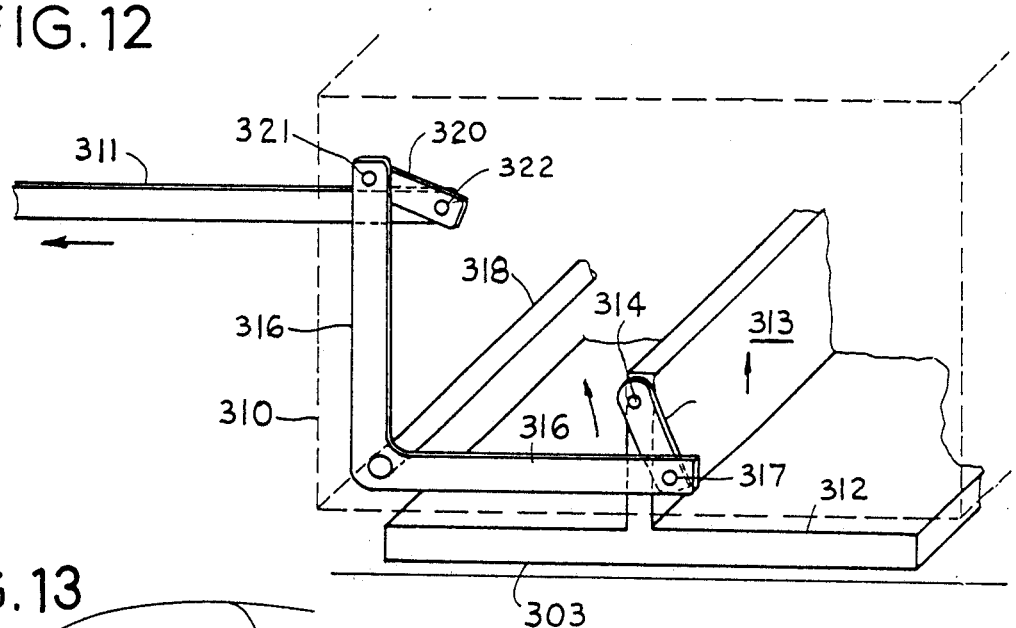
FIG.13
FIG.14
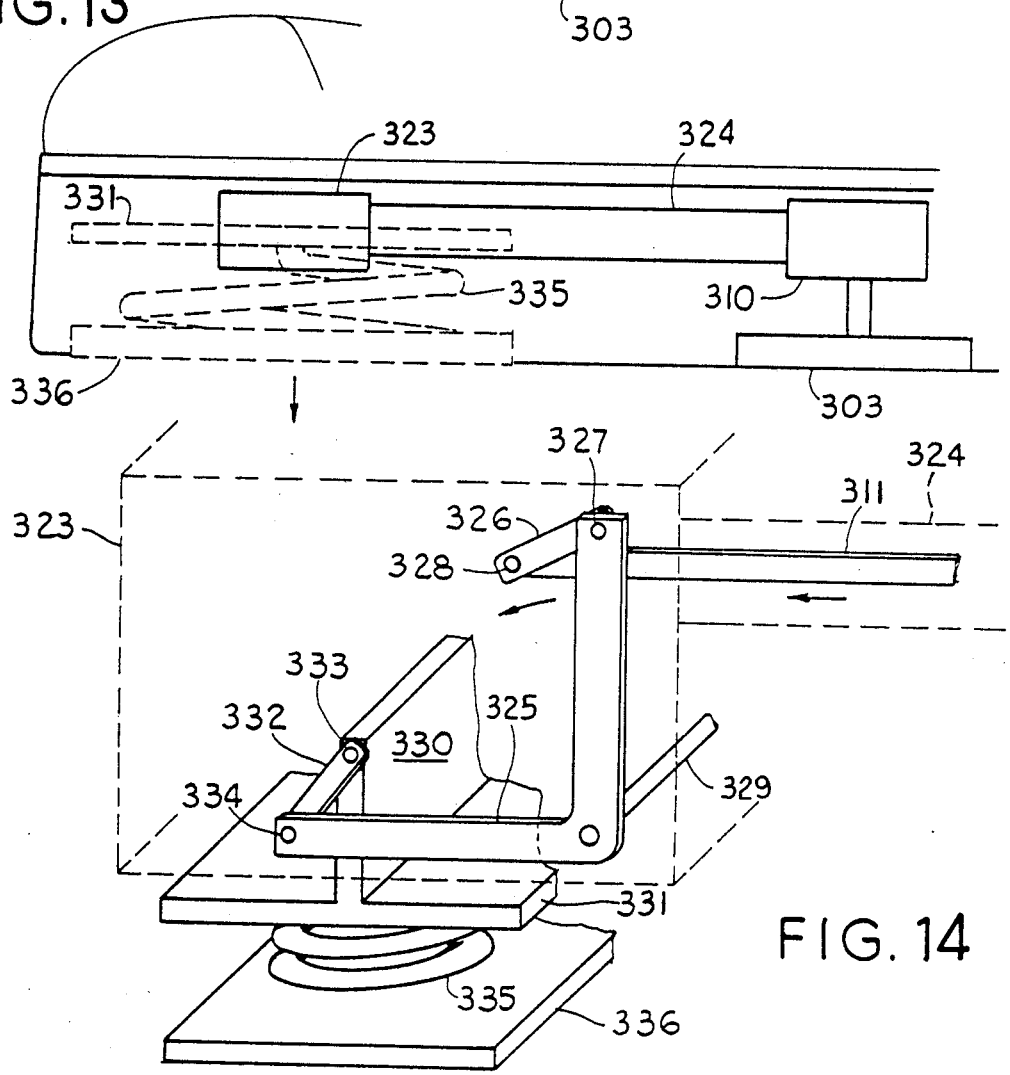

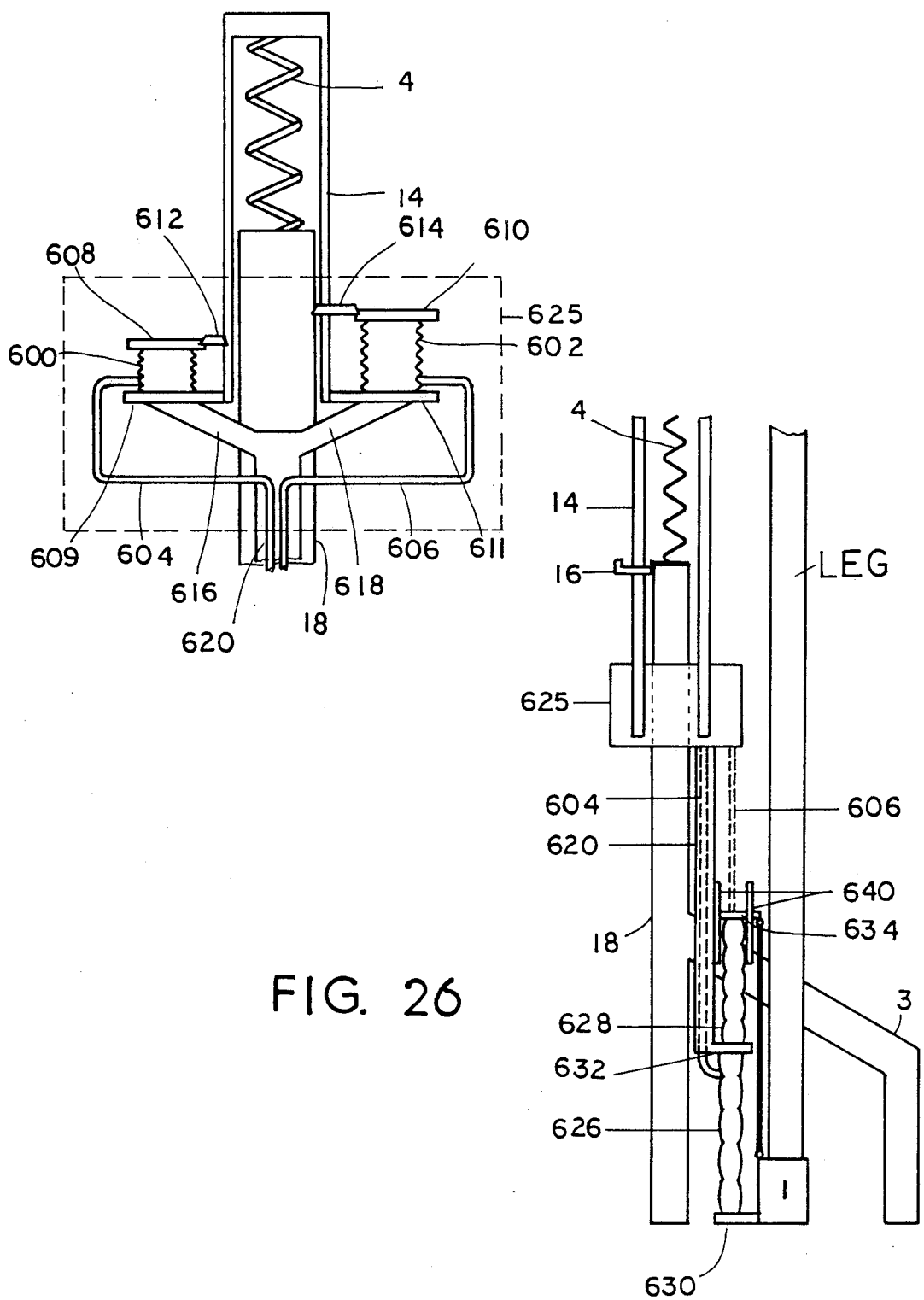

ENERGY-EFFICIENT RUNNING BRACE

This is a division of application Ser. No. 091,130 filed 8/31/87, now abandoned.

BACKGROUND OF THE INVENTION

This invention relates to running braces and in particular to energy-efficient running braces.

This invention augments the effective spring constant of the leg by adding a resilient brace which supports the runner's weight in parallel with the leg. Furthermore, it provides for a body brace to function as an exoskeleton to protect from impact shock to body organs and body connective parts such as the joints of the knees, back, and neck.

The act of running involves vertical motion of a runner's center of gravity. The lifting of the runner's weight requires muscle work. When the runner's foot impacts the ground, both the kinetic energy and the momentum associated with the vertical motion must be absorbed. Approximately 45% of the vertical kinetic energy is stored in the resilient parts of the leg and foot, with the remainder lost to the ground and the leg. The lost energy must be replaced by muscle work. This invention is intended to minimize lost energy or, equivalently, to maximize the energy efficiency of running.

Scientific inquiry of running includes the study of the efficiency of running as a function of various parameters. Researchers have been attempting to discover optimized running parameters for greater energy efficiency and to fewer injuries. Dr. Thomas A. McMahon of Harvard University discussed how the resiliency of tracks can be tuned to improve performance and safety in his article "Mechanics of Locomotion," T. McMahon, 3 Int. J. Of Robotics Research 4 (1984). One of his results is that running times improve by two or three percent and injuries are reduced by a factor of two when the effective spring constant of the track is approximately two times that of a runner's leg. Prior art running shoes cannot achieve improved energy efficiency equivalent to that achieved with tuned tracks, because impact is on the heel whereas take-off is from the toe. Prior art running shoes do not have a means for transmitting the impact energy from the heel to the toe.

Furthermore, the effective spring constant of a leg must be large to achieve high performance or speed. A drawback of tuned tracks is that the effective stiffness of the leg/track system is smaller than that of the leg itself, since the track acts as a spring in series with the spring representing the leg, and the spring constants of springs acting in series add reciprocally. The present invention solves that problem by having the braces act in parallel with the legs, in which case the spring constants add linearly.

Two important concepts are compliance and resilience. Compliance refers to the property of the sole to give or compress upon foot impact; resilience refers to the property of the sole to return to its original shape. This can be made clearer by referring to a spring model with damping. The term damping includes all friction losses. A spring system may be very compliant by virtue of having considerable damping, but then it is not energy efficient. Prior art running shoes have this drawback. The term resilience as used herein means that damping is minimized, so energy efficiency is maximized. In summary, compliance describes a system where impact energy dissipated, whereas resilience refers to a system where energy loss is conserved.

An example of an invention that provides compliance in a shoe is described in U.S. Pat. No. 4,446,634. This shoe has liquid-filled bladders under the heel and sole, and controls the heel compliance with an adjustable valve in between. Since provision is made for energy storage and release, however, this shoe would not be energy efficient.

U.S. Pat. Nos. 4,237,625 and 4,358,902 disclose energy-efficient shoes. These have liquid-filled bladders below the heel and ball of the foot and resilient material below these bladders. However, there is no provision to transmit the energy of heel impact to the front of the foot, to store it, and to release it during thrust. The only energy that might be returned during thrust is that stored in the resilient material below the front of the foot, and this would be a small portion of the impact energy. Accordingly, this shoe would not be very energy-efficient.

U.S. Pat. No. 4,451,994 discloses a shoe having a resilient mid-sole. This shoe cannot capture the heel-impact energy, nor can it give back much of the "mid-sole-impact" energy during thrust. U.S. Pat. No. 4,030,213 discloses a shoe with springs throughout the sole. This shoe may be compliant, but it would not be energy efficient, since there is no provision for transferring heel impact energy to the front of the shoe.

Leg-brace devices in prior art are called walking irons. U.S. Pat. No. 2,206,234, granted in 1940 and entitled an "Invalid Walking Aid Apparatus," has a brace which extends from the foot to the upper leg and it has a spring to cushion the impact of foot strike. However, contact with the ground is made via a pair of feet each of which is similar to the foot of a pogo stick. This device is appropriate for hobbling, whereas the present invention is intended for running because the foot strike involves the entire foot, thereby making possible better balance and stability. Another difference is that the cushion springs in the just-mentioned invention act in series with the effective springs of the legs, whereas the brace springs in this invention act in parallel, which results in a higher effective spring constant and greatly enhanced performance.

A important consideration is the protection of the connective parts of the upper body, mainly the back and neck, from impact shock transmitted through the leg brace, to the pelvis, and up the back. When the effective stiffness of the leg/brace system is high enough, the optional back and neck braces, and the accompanying shoulder and chin harnesses, are needed to act as an exoskeleton for the back and neck.

SUMMARY OF THE INVENTION

Accordingly, one object of the present invention is to provide a running brace for improved performance that will make running more enjoyable and satisfying.

Another object of the present invention is to provide a running brace that will reduce injuries.

A further object of the present invention is to provide a running brace that will provide a high level of energy efficiency and adequate safety on existing non-compliant surfaces, such as concrete.

Another still further object of the present invention is to provide a running brace that has the ability to dramatically reduce impact shocks on the foot and body to compensate for weakened body parts, with a concurrent significant increase in running speed and energy efficiency.

Another object of the present invention is to provide a running brace that corrects for orthopedic problems of the legs, back, and neck.

Another object of the present invention is to provide a running brace with a the structural design that is optimised in lightness and energy efficiency for development of artificial robotic legs.

Yet another object of the present invention is to make possible various recreation applications based on the ability to bound high into the air.

Other objects of the present invention will be apparent to those skilled in the art from the specification and drawings.

Briefly, in accordance with one embodiment of this invention, the foregoing objectives are achieved by providing a running brace with a structure that transmits the force and energy of the runner's impact from a pelvic harness to a storage means in said running brace. At the proper time this energy is released to contribute to the thrust of the runner off of the running surface. As a result, the balance and control capabilities of the foot/leg system are combined with the strength and resilience features of an artificial brace system.

BRIEF DESCRIPTION OF THE DRAWINGS

FIG. 5 is a perspective view of the first leg-brace embodiment of this invention, showing the star wheel gear used within the catch/release means.

FIG. 6 is a top view of the first leg-brace embodiment, showing the location of the front and rear forks on either side of the foot.

FIG. 12 is a three-dimensional view of the force-redirection mechanism used in the first energy-efficient sole embodiment for the second leg-brace embodiment of this invention.

FIG. 13 is a side view of the first energy-efficient sole embodiment for the second leg-brace embodiment of this invention, showing the transmission mechanism and the storage/thrust mechanism.

FIG. 14 is a three-dimensional view of the storage/thrust mechanism used in the first energy-efficient sole embodiment for the second leg-brace embodiment of this invention.

FIG. 25 is a side view of the upper part of the fifth leg-brace embodiment of this invention, showing the location of the hydraulic means for storing leg energy in the brace storage means during flight.

FIG. 26 is a front view of the lower part of the fifth leg-brace embodiment of this invention, showing the location of the hydraulic means for storing leg energy in the brace storage means during flight.

DETAILED DESCRIPTION OF THE PREFERRED EMBODIMENTS

Figure 1:
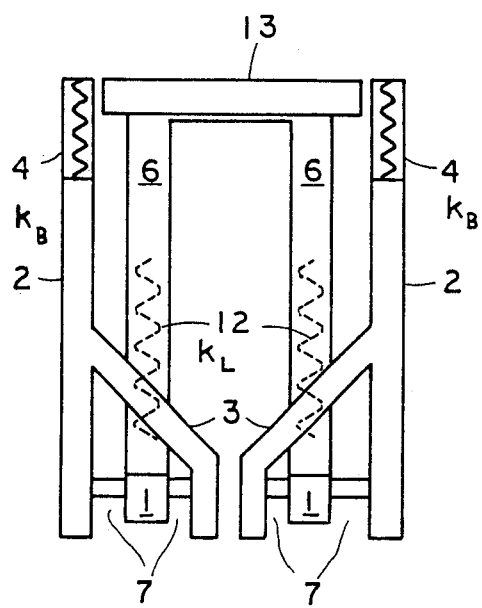
FIG. 1 is a front view of the first leg-brace embodiment of this invention.

The description of the invention is set forth hereafter in two parts. The first deals with various kinds of leg braces to support the leg while running; the second deals with harnesses used to attach the leg brace and additional back and neck braces to the body. These are necessary to protect the upper body from the greater impacts that will result from bounding higher into the air. Throughout the drawings the same reference numerals have been used for corresponding parts of the invention.

LEG BRACES

To improve running performance it is necessary to increase the effective spring constant of the leg. This results in a shorter foot-contact time, which means that the leg muscles work for a shorter time. Also, there is an increased proportion of flight time, as opposed to foot-contact time. For example, when an antelope pronks, it lands on all four legs (springs) at the same time (in parallel). Thus, its combined spring constant is four times that of a single leg, and that is the reason for its ability to maintain high speed. However, it is not possible to significantly change the leg spring constant, so another spring must be added in parallel to significantly improve performance.

Referring now to FIG. 1, prosthetic braces 2 on the outside and 3 on the inside of the runner's legs 6 support the impact force in parallel with her legs 6. These braces, henceforth referred to as leg braces, are rigidly attached to pelvic harness 13 at the top and to the soles 1 of the runner's shoe by axles 7. The downward slanting elements 5, connecting supports 2 with inner supports 3, consist of two parts, the first of which goes around the back of the leg and the second of which goes around the front. Springs 4 are part of the leg braces and have spring constants $k_B$. The resilient parts of the leg can be modeled by a spring 12 referred to heretofore as the leg spring, which has a spring constant $k_L$. Since the various springs act in parallel, their spring constants add linearly to give a combined spring constant, $k_C$, given by the formula $k_C = k_L + k_B$.

Since the force on each support element (the leg and the leg brace) is proportional to its spring constant, the portion of impact borne by the leg can be decreased by increasing the spring constant $k_B$ of the leg brace Doing so reduces the impact shock to the leg.

Figure 2:
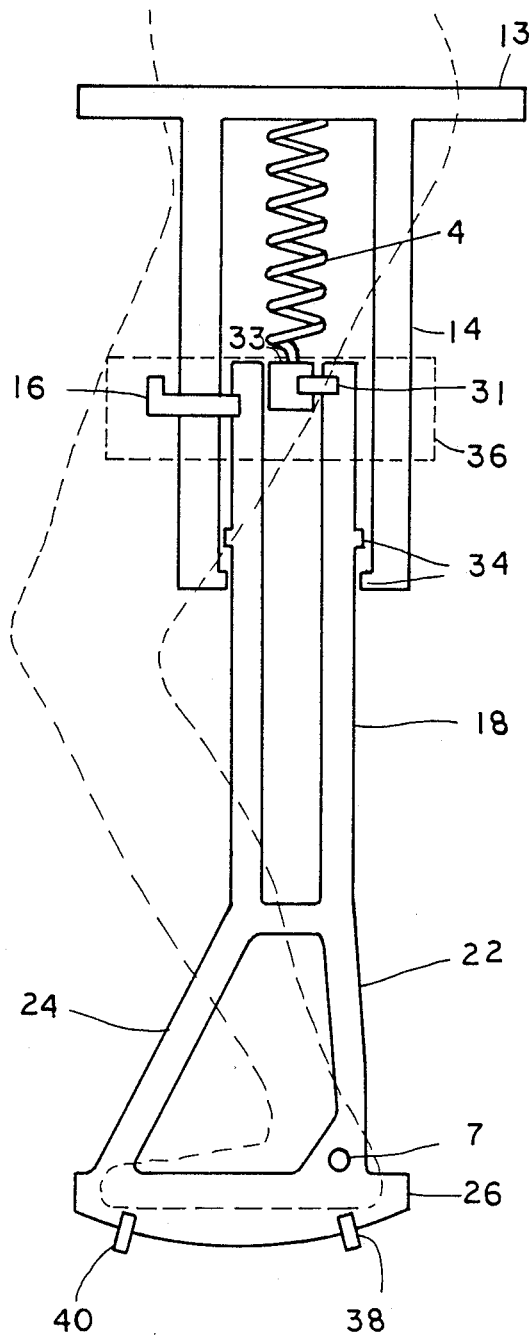
FIG. 2 is a side view of the first leg-brace embodiment of this invention, showing the location of the energy storage means.

The outside part of the first embodiment of the invention is shown in side view in FIG. 2. Upper brace 14 contains an energy storage device 4 which is compressed during impact by the upward motion of lower brace 18 within upper brace 14. This storage means may be any resilient material such as a helical spring or a resilient plastic. The top of said upper brace is rotatably attached to harness 13 at hip level. The lower part of lower brace 18 separates into front fork 24 and heel fork 22. The bottoms of said forks are connected to each other by rocker foot 26, and to the shoe sole by axle 7. The brace elements are constructed of a light strong material such as aluminum or plastic.

Figure 3:
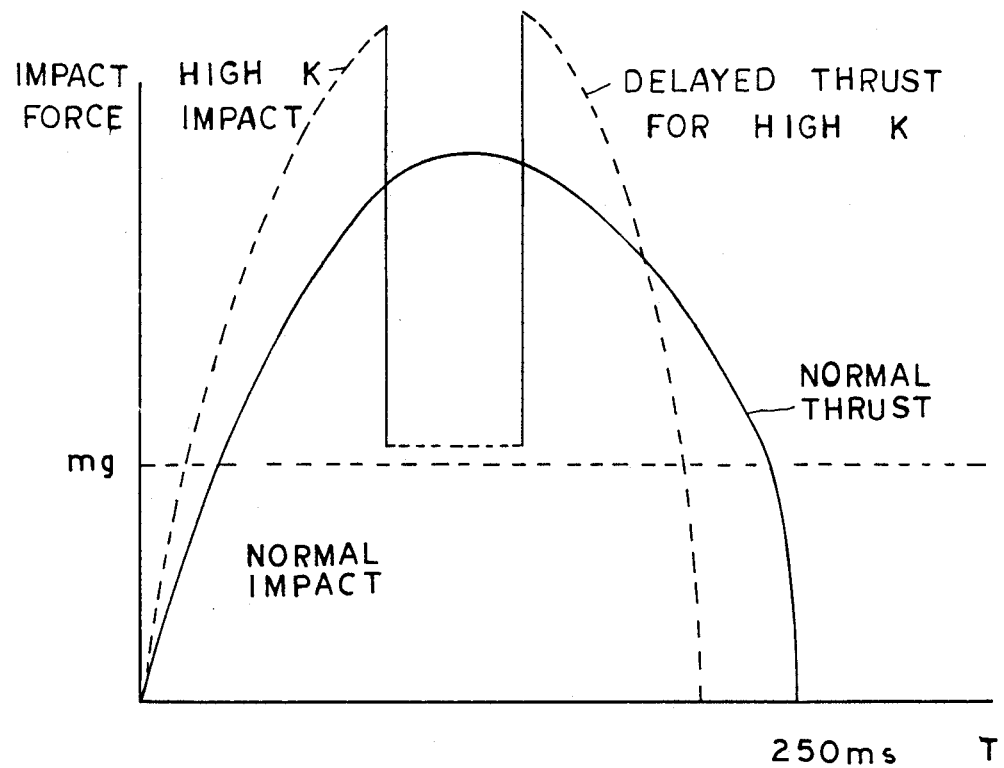
FIG. 3 is a "force versus time" curve showing a runner's foot impact and thrust with and without an intervening time delay.

The solid curve in FIG. 3 shows the impact force as a function of foot-contact time for the case where there is no delay between impact and thrust. Impact occurs when the curve is rising, and thrust occurs when it is falling. If the roll-over time (the time it takes for the foot to roll over from the heel to the toe) is less than the impact time, the thrust resulting from the expansion of the storage means would push the runner backwards. This limits the value of the storage means spring constant, since the impact time interval is inversely proportional to its spring constant. Thus, for high spring constant values (high performance), it is necessary to delay the storage means release; for low spring constants this delay is not necessary. The dashed curve in FIG. 3 shows that the force curve drops to a constant value equal to the runner's weight during the delay.

Figure 4:
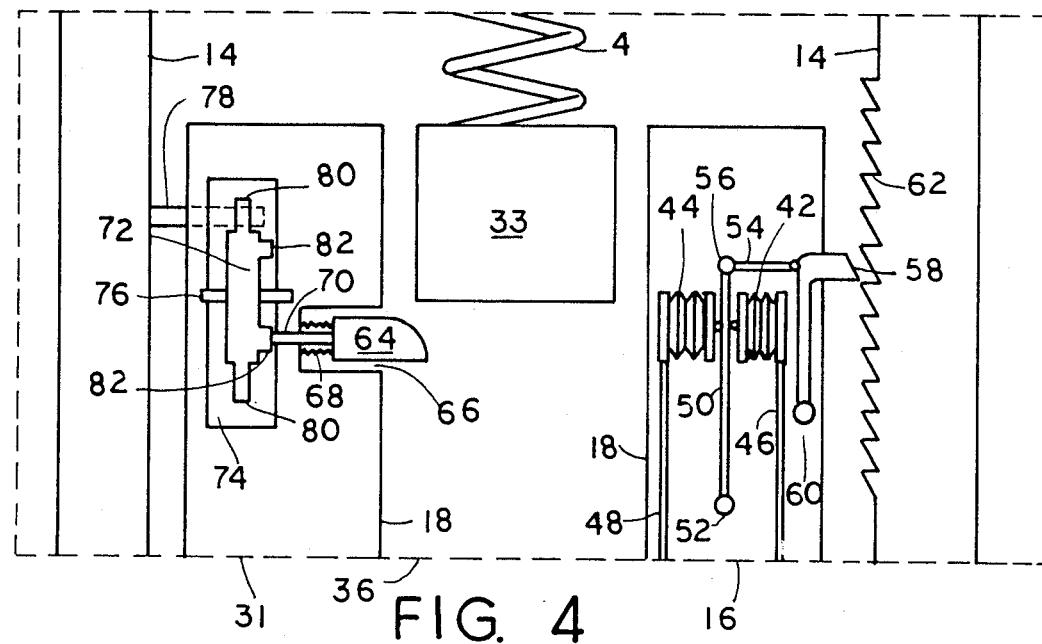
FIG. 4 is a side view of the first leg-brace embodiment of this invention, showing the location of the catch/release and ratchet/release means for the storage means.

Delay is achieved as follows. Conventional ratchet/release 16 in FIG. 2 ensures that lower brace 18 can only move up with respect to upper brace 14, thereby only compressing storage means 4, until ratchet/release 16 is released during thrust. One way to achieve this release is shown in FIGS. 2 and 4. Hydraulic means 40, such as a Sylphon bellows, located at the bottom of front fork 24 is connected by tube 46 to another hydraulic means 42 in ratchet/release means 16 in such a manner that the ground force on front fork 24 compresses hydraulic mechanism 40, sending fluid up connecting tube 46 and causing hydraulic means 42 to expand. This expansion causes link 50 to rotate counterclockwise about hinge 52, which causes link 54 (rotatably attached to link 50 by pin 56) to pull ratchet arm 58 (rotatably attached to link 54 at the top and to hinge 60 at the bottom) to disengage from ratchet teeth 62.

Ratchet arm remains disengaged until the next heel impact by the same foot, at which time hydraulic means 38 located at the bottom of heel fork 22 of FIG. 2 is compressed. This compression causes fluid to flow up tube 48 (in FIG. 4), causing hydraulic means 44 to expand, rotating link 50 clockwise and re-engaging ratchet arm 58 in ratchet teeth 62.

Other ways to activate this ratchet release are by a lever activated by the runner's hand or a conventional electrical means which senses the onset of force onto front forks 22 and 24 and sends an electrical signal to a battery powered relay, triggering release.

The same release mechanism 16 is used for braking. That is, when the runner wants to stop, a conventional lock is set, ensuring that ratchet/release 16 (FIG. 2) does not release storage means 4 for thrust and the runner stops.

FIGS. 4 and 5 depict catch/release means 31 (from FIG. 2). This mechanism allows the leg to bend while in flight by allowing lower brace 18 to disengage from spring plug 33, thereby allowing lower brace 18 to move up within upper brace 14 without having to work against storage means 4. Catch/release means 31 includes a six-sided star wheel gear 72 (shown in perspective view in FIG. 5) which rotates about axle 76 in cavity 74 within the wall of the upper portion of lower brace 18. Hinged bar 78 with rotatable end bar 79 is rigidly attached to upper brace 14. When lower brace 18 moves upward relative to upper brace 14, end bar 79 maintains the straight position illustrated in FIG. 5. As a result, star wheel gear 72 turns approximately 60 degrees counterclockwise (as viewed from the right side of FIG. 5). When lower brace 18 moves down relative to upper brace 14, end bar 79 bends down about hinge 88, so that star wheel gear 72 does not rotate. Hinge 88 only allows end bar 79 to bend downward. Recovery springs 90 return end bar 79 to its unbent position after every upward pass of lower brace 18. Thus, hinged bar 78 turns star wheel gear 72 by impelling each of the six gear spokes 80, in turn.

Again referring to FIGS. 4 and 5, raised surfaces 84 push drive pin 70 to the right, which drives catch 64 outward to engage spring plug 33 (see FIG. 2) with lower brace 18, allowing storage means 4 to be compressed during foot strike. Immediately after thrust, the upward motion of lower brace 18 relative to upper brace 14 (or equivalently the downward motion of hinged bar 78 with respect to gear spoke 80) causes star wheel gear 72 to rotate so that the next lowered surface 86 impinges against drive pin 70. This allows recovery springs 68 to pull catch 64 into cavity 66, thereby disengaging lower brace 18 from spring plug 33. Thus, the leg can then bend in flight and clear the ground while it is being brought forward for its next foot strike. At that time hinged bar 78 moves down again causing the next raised surface 84 to push catch 64 out to catch spring plug 33 so that storage means 4 is compressed during impact.

It should be understood that there might be more than one set of each of catch/release means 31 or the ratchet/release means 16, and that the dimensions of ratchet arms 58 and catches 64 in the direction perpendicular to the plane illustrated in FIG. 4 may be as large as is required to support the impact forces involved. It should be further understood that the hydraulic means (38 and 40 in FIG. 2 and 42, 44, 46, and 48 in FIG. 4) could be replaced by a system of cables and bent levers, in a conventional manner, for the purpose of engaging and disengaging ratchet/release means 16.

FIG. 6 is a cut-away top view of the bottom portion of leg brace 18 showing the cross-section of the inside pair of fork elements 30 and 32 and the outside pair 22 and 24. Inside fork elements 30 and 32 are mounted to member 18 by braces 3, as shown in FIG. 1. Both axle 7 and inside fork elements 30 and 32 are not absolutely necessary but can be included for stability. The four fork elements are quadrilaterally arranged around each foot. Forks 22 and 24 are connected by curved foot 26, and forks 30 and 32 are connected by curved foot 28. Curved feet 26 and 28 are covered with a soft rubber-like material to prevent damage to running surfaces. Rear forks 22 and 30 are rotatably connected to the shoe sole by axle 7, which passes through the sole, so that the front of the sole is free to rotate around the axle. Thus, the toes can push against the ground, both to balance the runner and to deliver thrust during take-off. Feet 26 and 28 are located at a level slightly below the heel sole, so that the initial impact is borne by the leg brace.

Referring again to FIG. 2, upon impact, feet 26 and 28 transmit the impact force to storage means 14 through heel forks 22 and 30, respectively Slightly later, the runner's heel strikes the ground and the knee begins to bend, as shown in FIG. 2. The objective is to store most of the impact energy in storage means 14 where it will be available to impart thrust during take-off. The runner will control the proportion of impact borne by the leg by bending it faster or slower.

After heel strike, the foot rolls onto its front and the forward portion of feet 26 and 28 contact the running surface. Feet 26 and 28 are curved to ensure a smooth roll over. After roll-over, ratchet/release 16 releases and storage means 4 expands, thrusting the runner forward and into the air. This thrust is delivered through the front forks 24 and 32. After thrust, lower brace 18 has returned to its original position with respect to upper brace 14. It is prevented from falling out of upper brace 14 by stops 19.

Since the leg brace is attached to the runner only at the hip and the ankle, the knee is free to bend, which allows the runner to control the proportion of force borne by the leg brace, balance herself during impact, and thrust against the ground during take-off. Axle 7 makes possible the second and third of these actions. The energy efficiency objective is best served by minimizing leg work during impact and minimizing the damping in storage means 4. Leg and foot extension during take-off imparts energy into the leg/mechanical system to replace lost energy and to run faster.

Figures 7, 8:
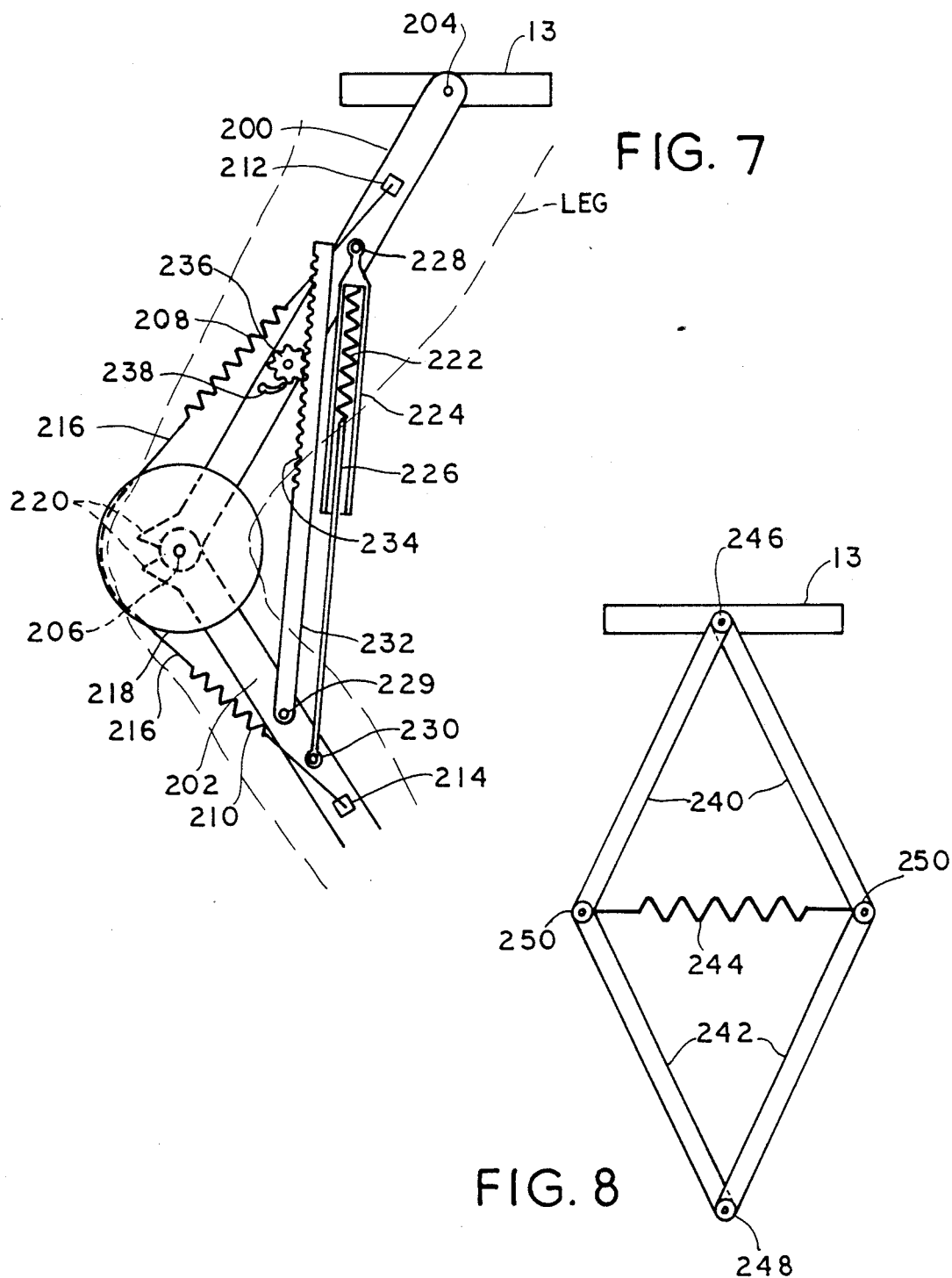
FIG. 7 is a side view of the second embodiment of a support means and a storage means of the first leg-brace embodiment of this invention, showing the locations of springs which resist the bending of a hinged leg brace.
FIG. 8 is side view of the third embodiment of a support means and a storage means of the first leg-brace embodiment of this invention, showing the locations of springs which resist the bending of a pair of opposed hinged leg braces.

FIG. 7 shows a second embodiment of the storage means of FIG. 2 which allows the leg brace to shorten during impact by the bending of upper brace link 200 and lower brace link 202 about axle 206. Upper brace link 200 is rotatably attached to pelvic harness 13 at swivel 204, and lower brace link 202 is attached to forks 22 and 24 and rocker feet 26 as shown in FIG. 2. Upper extender spring 208 is attached at one end to upper brace link 200 at point 212 and at its other end to cable 216. Lower extender spring 210 is attached at one end to lower brace link 202 at point 214 and at its other end to cable 216. Both upper extender spring 208 and lower extender spring 210 resist the bending of upper brace link 200 with respect to lower brace link 202, in tension, in a manner similar to the action of a runner's tendons and muscles. The component equivalent to tendons is cable 216 which wraps around pulley 218 as the leg bends. Pulley 218 is also mounted on axle 206. Tabs 220 prevent upper brace 200 and lower brace link 202 from bending past the straight position when they bend back during take-off. Alternatively, resistance to bending can be accomplished by a spring acting in compression.

Upper flexion brace 224 is a hollow tube rotatably attached to upper brace link 200 at point 228. Lower flexion brace link 226 is rotatably attached to lower link 202 at point 229 and moves upward within upper flexion brace 224 during impact, compressing flexion spring 222, which resists the impact force.

The catch/release and ratchet/release means of the first leg-brace embodiment are used in a similar manner for this second embodiment of the storage means, except that the mounting is as shown in FIG. 7. Rack 232 is rotatably attached to lower brace link 202 at 229 and constrained to engage and turn pinion 236 as it moves upward with respect to this pinion while the leg bends. Pinion 236 is rotatably attached to upper brace link 200, as is pawl 238, which is used to achieve intermittent ratchet and release as in the embodiment of FIG. 2.

FIG. 8 shows a third embodiment of the storage means of the first leg-brace embodiment. In place of the single set of bending links of FIG. 7, there are two opposing sets comprising a pair of upper brace links 240 rotatably attached to a pair of lower brace links 242 by pins 250 and rotatably attached to pelvic harness 13 by pin 246. The opposite ends of links 242 are attached together by pin 248. The pair of lower brace links 242 are rotatably attached to a lower brace similar to the bottom of lower brace 18 of FIG. 2, with forks and rocker feet. Cross spring 244 resists the bending of upper brace links 240 with respect to lower brace links 242 during impact, in extension.

The storage means of FIGS. 2, 7 and 8 resist the impact force as distinct functions of the change in vertical height of the runner's center of mass, with the latter two storage means having terms proportional to trigonometric functions in these impact force functions. Use of various combinations of these three storage means, therefore, affords greater versatility in achieving optimal impact force curves.

The first leg-brace embodiment of FIGS. 1–8 allows the heel to absorb part of the impact shock. This results in energy loss since there is no provision to transmit the impact energy to the front of the runner's foot where it might contribute to thrust during take-off. The second embodiment of the leg-brace invention utilizes the same leg brace and, in addition, utilizes an energy-efficient sole mechanism to prevent the energy associated with the heel impact from being lost. This sole mechanism, described more fully hereafter, transmits the heel impact force to the front of the sole, stores the associated energy by compressing a resilient device, and releases this energy, thrusting the runner back into the air.

Figure 9:
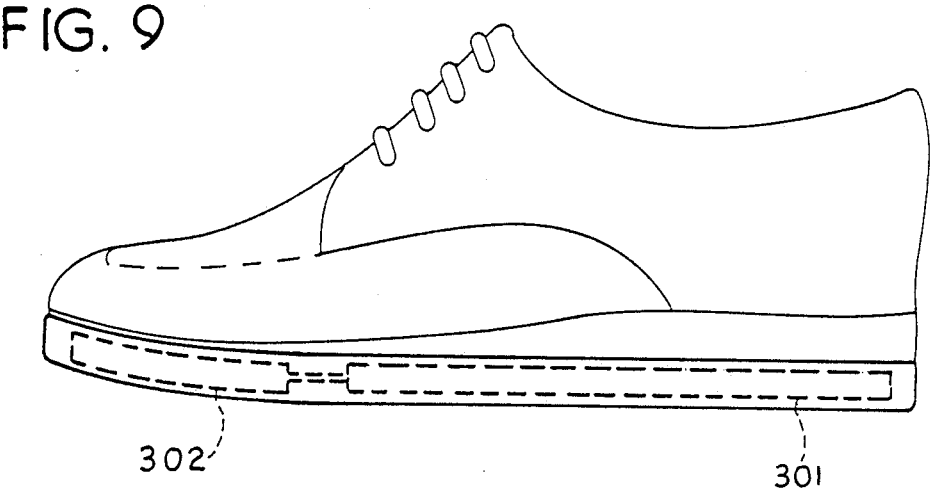
FIG. 9 is a schematic side view of the first energy-efficient sole embodiment for the second leg-brace embodiment of this invention, showing the location in the shoe sole of the transmission mechanism and the storage/thrust mechanism.

FIG. 9 is a schematic representation of the energy-efficient sole mechanism, showing the location of a transmission mechanism 301, which re-directs the runner's heel impact force and transmits it to the front of the sole, and a storage/thrust mechanism 302, which stores the energy of the heel impact force below the front of the foot and releases it to contribute to the thrust which propels the runner back into the air.

Figure 10:
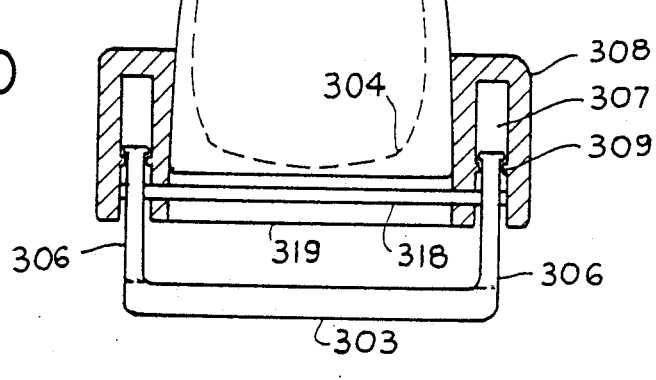
FIG. 10 is an end view of the heel portion of the first energy-efficient sole embodiment for the second leg-brace embodiment of this invention, showing the transmission mechanism.

Referring now to FIG. 10, heel force plate 303, which is positioned under the runner's heel 304, receives the force of heel impact on running surface 305. Heel force plate 303 has four vertical guide bars 306, arranged in a quadrilateral configuration about heel 304, which move perpendicular to the running surface in channels 307 in anti-tilt housing 308. This ensures that heel force plate 303 does not tilt or bind, even when the impact force of the ground is not centered on it. Stops 309 on guide bars 306 prevent the guide bars from exiting channels 307.

Figure 11:
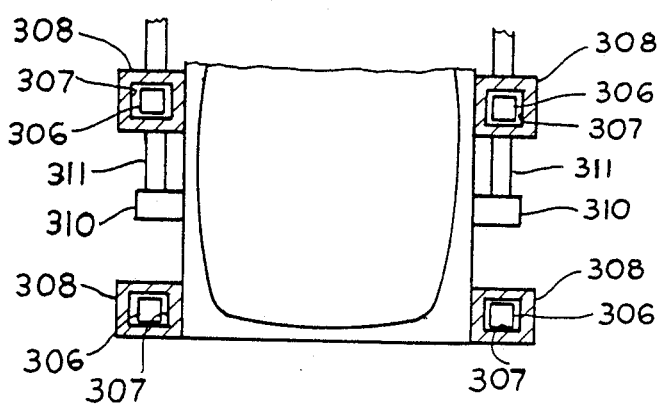
FIG. 11 is a top view of the heel portion of the first energy-efficient sole embodiment for the second leg-brace embodiment of this invention.

FIG. 11 more clearly illustrates anti-tilt housing 308, and guide bars 306 and channels 307 contained therein. As further shown in this figure, force re-direction mechanism 310, which is driven by the upward motion of heel force plate 303, causes drive shafts 311, positioned at opposite sides of the sole, to move forward toward the toe of the running shoe, thereby transmitting the heel impact force to the front of the sole.

One end of force re-direction mechanism 310 is shown in greater detail in FIG. 12. It should be noted that the other end of this mechanism has the same component parts and operates in the same manner as described hereinafter. Heel force plate 303 comprises horizontal plate 312, whose bottom is covered with a conventional running shoe material such as Vibram, and raised plate 313 aligned perpendicular to plate 312. Pin 314 is attached to the top portion of raised plate 313 and extends slightly beyond the side edge thereof. Hinged link 315, located along side the end of vertical plate 312, is rotatably fastened to pin 314. The other end of hinged link 315 is rotatably fastened at the end of one arm of conventional bent lever 316 by pin 317. Bent lever 316 is rotatably fastened to an axle 318 at the junction point of its two arms.

Referring again to FIG. 10, axle 318 passes through and is embedded in sole 319 of the running shoe, so that it does not move relative to sole 319. The upper arm of bent lever 316 is rotatably fastened to a second hinged link 320 by pin 321. The other end of hinged link 320 is rotatably fastened to drive shaft 311 by pin 322.

When heel force plate 303 strikes running surface 305, the impact force causes it to move upward toward heel 304 and sole 319. Since axle 318 is not free to move relative to sole 319, the upward movement of heel force plate 303 causes hinged link 315 to move upward and bent lever 316 to rotate in an arc in a counterclockwise direction. It should be understood that the corresponding bent lever on the opposite end of heel force plate 303 will rotate in the same direction as bent lever 316. Raised plate 313 is used because hinged link 315 must pull rather than push. The counterclockwise rotation of bent lever 316 pulls hinged link 320 towards the toe of the shoe, thereby forcing drive shaft 311 to travel in the same direction. Hence, it will be seen that hinged link 320 converts the circular arc motion of bent lever 316 to the straight-line motion of drive shaft 311. It also should be noted that the two legs of bent lever 316 may be of different lengths in order to provide mechanical advantage to force-redirection mechanism 310.

Referring now to FIG. 13, drive shaft 311 is coupled at its front end to another force re-direction mechanism 323. Drive shaft 311 is contained in a shaft housing 324, which constrains it to travel forward and rearward in a straight line. It should be understood that an identical drive shaft and shaft housing are located on the opposite side of the shoe.

Referring now to FIG. 14, drive shaft 311 is connected to bent lever 325 by conventional hinged link 326. Hinged link 326 is rotatably fastened to the upper arm of bent lever 325 by pin 327, and rotatably fastened to drive shaft 311 by pin 328. An axle 329 passes through bent lever 325 at the junction of its two arms and is rigidly mounted in the forward portion of sole 319 so that bent lever 325 can rotate around it. The lower arm of bent lever 325 is connected to raised plate 330 of storage plate 331 by hinged link 332. Hinged link 332 is rotatably connected to raised plate 330 by pin 333 and rotatably connected to the lower arm of bent lever 325 by pin 334. Storage plate 331 is rigidly connected to one end of helical storage means 335. The other end of storage means 335 is rigidly attached to thrust force plate 336, which contacts running surface 305 and, like heel force plate 303, has its bottom covered with a conventional running shoe sole material such as Vibram. Alternatively, multiple springs, resilient plastic, or an elastomer can replace storage means 335, thereby providing an advantage in durability or weight. When drive shaft 311 is driven forward by force re-direction mechanism 310, bent lever 325 rotates in a counterclockwise direction around axle 329, moving storage force plate 331 downward and compressing storage means 335.

Ideally, storage means 335 obeys a force law $F = kx^Y$, where y is less than 1.0 and held as small as possible, k is the spring constant of storage means 335, and x is the distance travelled by storage means 335 from its uncompressed position to its compressed position. Alternatively, storage means 335 may be pre-compressed, in which case $F = Fo + kx$, where Fo is the pre-compression force.

Figure 15:
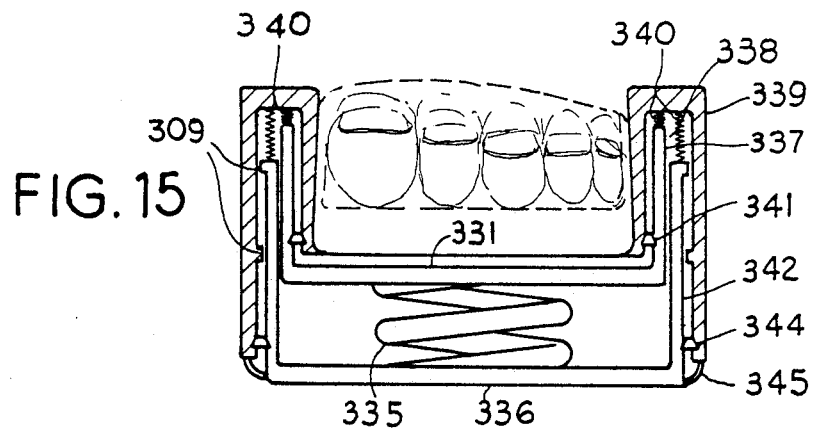
FIG. 15 is a front view of the toe portion of the first energy-efficient sole embodiment for the second leg-brace embodiment of this invention, showing the storage/thrust mechanism.
Figure 16:
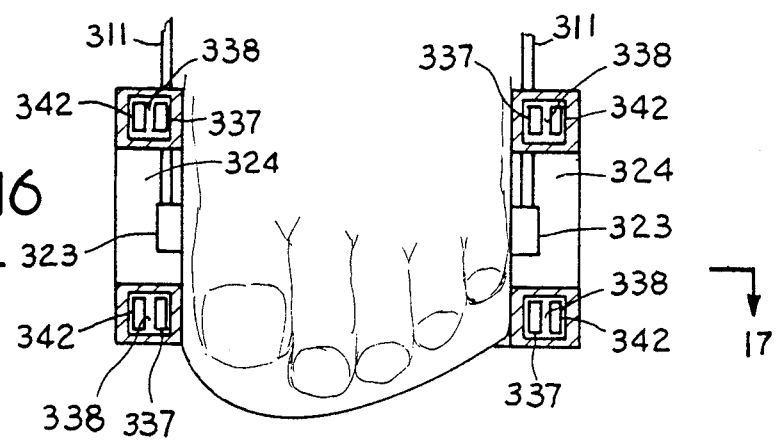
FIG. 16 is a top view of the toe portion of the first energy-efficient sole embodiment for the second leg-brace embodiment of this invention, showing the storage/thrust mechanism.

Referring now to FIGS. 15 and 16, storage force plate 331 is fixably attached to four guide bars 337 arranged in a quadrilateral pattern around the toe portion of the running shoe. Guide bars 337 move perpendicular to storage force plate 331 in channels 38 contained in anti-tilt housing 339. The top portion of each guide bar 337 is connected by a storage means 340 to said housing at the top of its corresponding channel 338. Storage means 340 have minimal resistance and thus require a minimum amount of energy to stretch. A conventional ratchet device 341 is attached between housing 340 and guide bar 337, allowing storage force plate 331 to move downward but not upward. This ensures that the impact energy stored in storage means 335 is not lost by the upward movement of force plate 331. It will be seen that such upward movement would move drive shafts 311 rearward, resulting in the re-transmission of the impact energy back to heel 304.

Compression of storage means 335 by storage force plate 331 continues for the duration of the heel impact interval. Storage means 335 is also compressed from the bottom by thrust force plate 336 during the period of toe impact. Thrust force plate 336 has four guide bars 342, each of which shares a channel 338 with a guide bar 337 from thrust force plate 331. Alternatively, anti-tilt housing 339 has separate channels for guide bars 337 and 342. Four conventional ratchet devices 344, each of which is mounted to the exterior wall of one of channels 338, prevent thrust force plate 336 from moving downward against the running surface until released, as described with reference to FIG. 17 below. This ensures that any toe impact energy is stored until thrust. Ratchets 344 are released at the beginning of the thrust interval, allowing storage means 335 to expand to its uncompressed state and causing thrust force plate 336 to push against the running surface, thereby aiding the runner's propulsion into the air.

Figure 17:
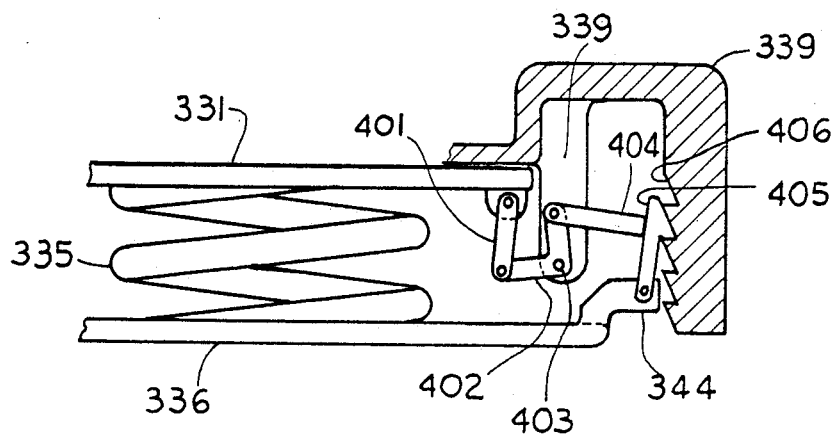
FIG. 17 is a side view of the ratchet/release mechanism used in the first energy-efficient sole embodiment for the second leg-brace embodiment of this invention.

Ratchet mechanism 344 is shown in FIG. 17. Ratchet release is determined by the relative spacing between storage force plate 331 and anti-tilt housing 339. Hinged link 401 is rotatably mounted at one end to the bottom of storage force plate 331 and rotatably mounted at the other end to the bottom arm of bent lever 402. Bent lever 402 is rotatably mounted at the junction of its two arms to axle 403, which is fixably attached to the inner surface of anti-tilt housing 339. The upper arm of bent lever 402 is rotatably mounted to one end of hinged link 404, and the other end of hinged link 404 is rotatably mounted to conventional ratchet arm 405. This latter attachment point is vertically lower than the former attachment point and remains so throughout the range of movement of hinged link 404. The other end of ratchet arm 405 is rotatably mounted to the outer surface of guide bar 342. Ratchet teeth 406 are formed at the bottom portion of anti-tilt housing 339 so that ratchet arm 405 can engage each tooth as it moves upward.

As storage means 335 is compressed and force plates 331 and 336 move toward each other, hinged link 401 moves downward relative to axle 403, causing bent lever 402 to rotate counter-clockwise. This rotation causes hinged link 404 to move toward storage means 335, thereby pulling ratchet arm 405 away from teeth 406. When force plates 331 and 336 are sufficiently close, ratchet arm 405 disengages from ratchet teeth 406, allowing storage means 335 to expand to its uncompressed state and causing storage force plate 336 to move downward.

Said ratchet arm remains disengaged until, after thrust, the action of aforementioned recovery springs 340 of FIG. 13 cause storage force plate 331 and thrust force plate 336 to return to their pre-impact positions, with respect to anti-tilt housing 339. In order for said recovery springs to have effect, ratchets 341 must be released, allowing the storage force plate to move upward. This is accomplished with a similar ratchet release mechanism as that shown in FIG. 17, except that the release is keyed to the relative motion of storage force plate 331 and thrust force plate 336; so, when said thrust force plate expands to its original position with respect to said storage force plate, said release occurs. This, in turn, causes bent lever 325 (shown in FIG. 14) to return to its original position, which in turn moves bent lever 316 (shown in FIG. 12) to its original position and heel force plate 303 to its original position in preparation for the next heel impact.

Alternatively, a conventional, electronic device may be used to measure the relative velocity between force plates 331 and 335. When the velocity becomes zero, this device releases ratchet 344. Or, the release could occur after a fixed delay Although this method possibly provides more optimized timing of the release, it has the disadvantage of requiring battery power.

It should be understood that the entire force re-direction mechanism of FIGS. 12 and 13 could be incorporated into the sole of the shoe, with the accompanying restriction that the sole must be thicker and/or the allowed travel of the force-plates smaller.

Figure 18:
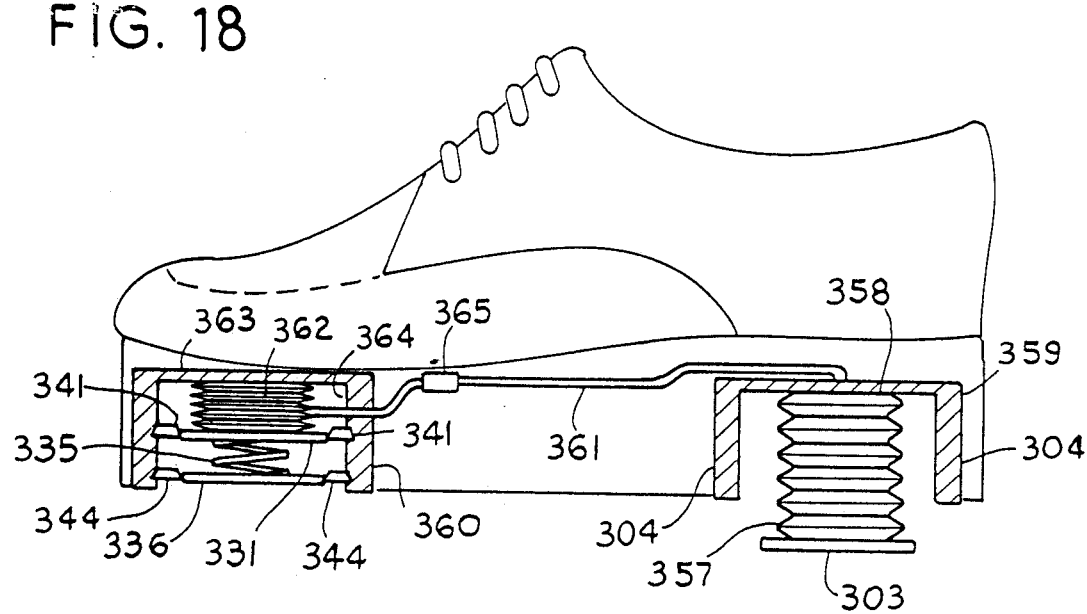
FIG. 18 is a side view of the second energy-efficient sole embodiment for the second leg-brace embodiment of this invention, showing the transmission mechanism and the storage/thrust mechanism using Sylphon bellows.

FIG. 18 illustrates a second embodiment of the energy-efficient sole. It uses hydraulics to convert the heel impact energy to toe thrust energy. Conventional Sylphon bellows 357 are attached at one end to heel force plate 303 and at the other end to wall 358 which is parallel to heel force plate 303 and which is located in heel housing 359. Bellows 357 is constrained to move perpendicular to the running surface by guide bar 306 and channels 307 (as shown in FIG. 11 attached to heel force plate 303. A tube 361 is attached at one end to the top of bellows 357 through a hole in wall 358 and at the other end to a second Sylphon bellows 362 in the toe portion of the sole. The top portion of Sylphon bellows 362 is attached to a wall 363 in housing 364, and the bottom portion of Sylphon bellows 362 is attached to storage force plate 331. As described above with respect to FIGS. 14 and 15, the bottom portion of storage force plate 331 is attached to the top end of storage means 335 and the bottom end of storage means 335 is attached to thrust force plate 336. Sylphon bellows 357 and 362 are filled with oil and change volume in the vertical direction when only compressed.

Upon heel impact, heel force plate 303 compresses bellows 357 against wall 358. This causes oil to flow through tube 361, which is just large enough to avoid significant viscous friction from oil flow due to the sudden impact. Oil emerging from the other end of tube 361 causes bellows 362 to expand, which in turn moves storage force plate 331 downward and compresses storage means 335. Conventional catch mechanisms 341 and 344 operate in the same manner as described above with respect to FIGS. 15 and 17 to allow thrust force plate 336 to move downward to aid take-off thrust and to prevent storage force plate 331 and thrust force plate 336 from returning to their rest positions until after the shoe is in mid-air. A conventional one-way valve 365 prevents the oil, and hence the heel impact force, from returning to the heel until after thrust, at which time a conventional release mechanism, keyed to the return of thrust force plate 336 to its uncompressed position with respect to storage force plate 331 (as in the case of FIG. 17), opens valve 365 and allows the oil in bellows 357 and 362 to return to their original pre-impact positions. It should be seen that it is still necessary to have an anti-tilt housing mechanism in this embodiment similar to that discussed in connection with the first embodiment of the energy-efficient sole of FIGS. 9-17.

This second embodiment of the energy-efficient sole illustrated in FIG. 18 has the advantage of eliminating certain moving parts, such as the bent levers and drive shafts. Another advantage is that considerable force can be accommodated hydraulically.

The third and forth leg-brace embodiments store energy sequentially in separate leg-brace storage means in such a manner that the impact force never exceeds a specified maximum value.

Figure 19:
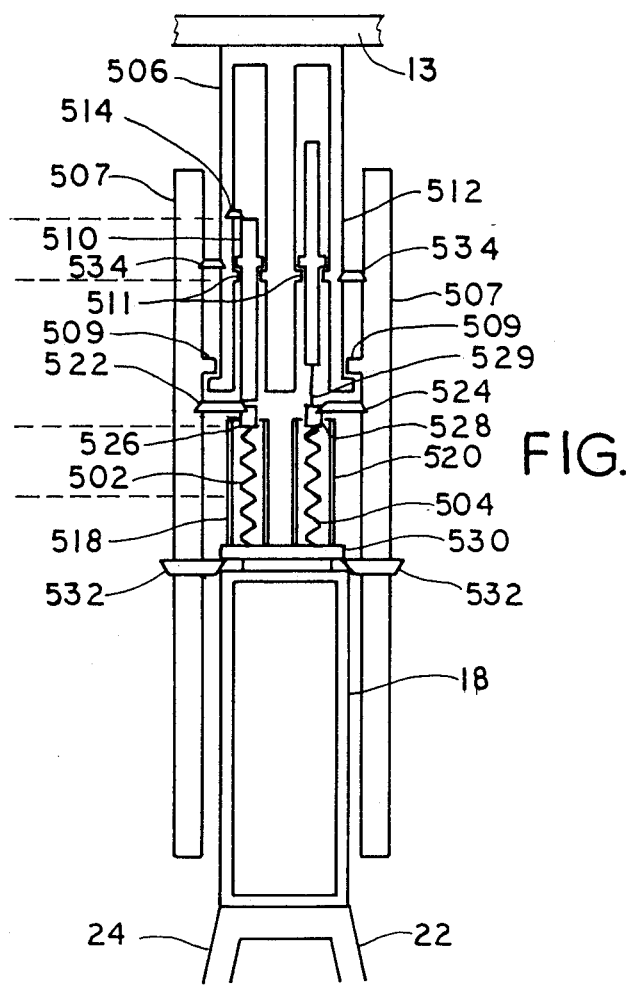
FIG. 19 is a side view of the third leg-brace embodiment of this invention, showing the location of two sequenced storage means.

FIG. 19 illustrates schematically the third leg-brace embodiment. In this embodiment, storage means 4 of FIG. 2 is replaced by two or more storage means 502 and 504. This configuration limits the impact force of the foot on the running surface by switching from one storage means to the next when the impact force reaches a prescribed value. Doing so limits the impact or shock felt by the skeleton to a particular value, e.g., 25 percent over the runner's body weight.

The sequential drive mechanism to compress the sequenced storage means one at a time is shown in FIG. 19. It comprises multiple channel 506 which is rigidly attached to pelvic harness 13 at its top. Housing 506 moves up and down inside outer brace 507 and is connected to spring drives 510 and 512 by ratchet/release catches 514 and 516. Spring drives 510 and 512 push down on storage means 502 and 504, respectively, by means of plugs 526 and 528. As in the first embodiment, the storage means may be any resilient material such as a helical spring or a resilient plastic. Plug 526 is rigidly attached to the bottom of spring drive 510, and plug 528 is attached to the bottom of spring drive 512 by cable 529 of length $x_o$. This ensures that plugs 526 and 528 will return to their pre-impact position before the next impact. Storage means 502 and 504 are constrained to move vertically and not to buckle by guides 518 and 520, respectively. Guides 518 and 520 fit inside multiple channel housing 506 so as not to impede its downward motion. Storage means 502 and 504 move force plate 530 downward when catches 532 release and catch 534 catches. Force plate 530 pushes against lower brace 18 which, in turn, pushes against front forks 24 and 32 and rear forks 22 and 30, in the manner described in FIGS. 2 and 4 for the first leg-brace embodiment.

Figure 20:
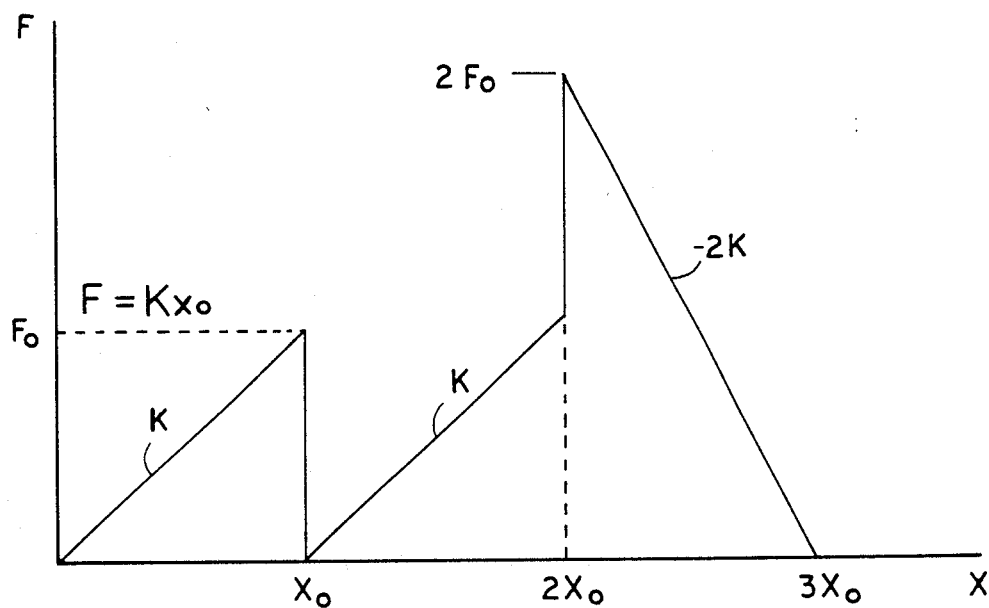
FIG. 20 shows a "force versus time" curve for the third embodiment of this invention.

Upon heel impact, multiple channel 506 of FIG. 19 receives the impact force from pelvic harness 13 causing spring drives 510 and 512 to move downward relative to lower brace 18, thereby compressing storage means 502 and 504. Spring drive 510 is located a fixed distance $x_o$ vertically lower than spring drive 512 by catch 514, and thus storage means 502 is compressed a distance of $x_o$ at the time spring drive 512 begins to compress storage means 504. At that time the force on storage means 502 is $F_o$, determined by the formula $F_o = kx_o$, where k is the spring constant of storage means 502, corresponding to the top of the first ramp in FIG. 20. At this time catch 514, which until this time has prevented spring drive 510 form moving up within multiple channel 506, releases, causing the force exerted on storage means 502 to decrease to zero as shown in FIG. 20. Beginning at this time, compression of storage means 504 by spring drive 512 causes the force curve to increase up the second ramp in FIG. 20 as multiple channel housing 506 continues downward relative to lower running brace 18.

Assuming that the impact energy equals $kx_o$, the impact is completely absorbed when the second ramp reaches the value $F_o$. Prior to that time ratchet/release means 522 and 524 have prevented storage means 502 and 504 from returning to their uncompressed state, as a result of which the impact energy is stored in storage means 502 and 504.

At the end of impact and the beginning of thrust, catch 532 releases and catch 534 catches, as described hereinafter, causing storage means 502 and 504 to simultaneously give a powerful downward thrust to force plate 530 and lower brace 18. This, in turn, causes an equal and opposite force to be exerted upwards against pelvic harness 13, propelling the runner back into the air. This is illustrated by the downward ramp from $2F_o$ in FIG. 20.

After thrust, catches 534, 522 and 524 release, allowing outer brace 507 to fall back to its original position with respect to multiple channel housing 506, allowing spring drives 510 and 512 to fall back to their original positions with respect to multiple channel housing 506, and allowing plugs 526 and 528 to fall back to their original positions with respect to multiple channel housing 506. It should be understood that plug 526 is rigidly attached to the bottom of spring drive 510 and plug 528 is attached to the bottom of spring drive 512 by cable 529. Also, outer brace 507 is prevented from falling further than its original position by stops 509 and spring drives 510 and 512 are prevented from falling further than their original positions by stops 511.

There are many conventional ways to achieve the catch means or the ratchet/release means. Catches 514 and 516 release after spring drives 510 and 512 have moved a prescribed distance with respect to multiple channel housing 506, and they re-engage after these elements have returned these elements to their original positions. The release of catches 532 and the simultaneous engagement of catches 534 are keyed to the roll-over onto front forks 24 and 32, as described with regard to ratchet/release 16 of the first leg-brace embodiment in FIGS. 2 and 4, while the respective re-engagement and release of said catches 532 and 534 are keyed to the end of thrust, as described in regard to FIGS. 2-5. Ratchet/release means 522 and 524 initially allow plugs 526 and 528 to move downward only, with respect to outer brace 507. After thrust, ratchet/release means 522 and 524 are released allowing these plugs to return to their original positions, again as described in regard to ratchet/release 16 in FIGS. 2 and 4.

Figure 21:
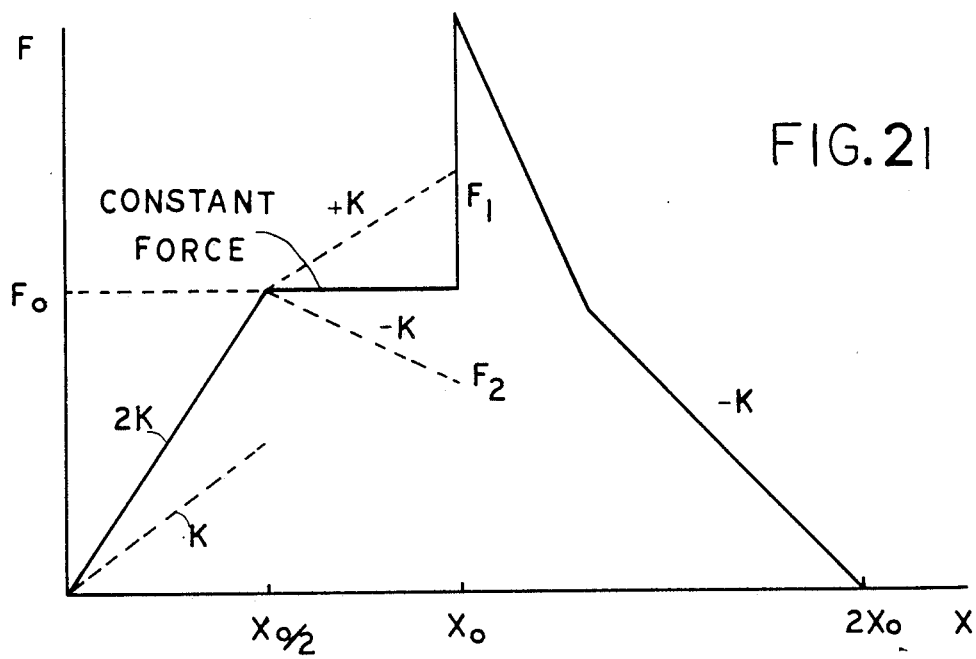
FIG. 21 shows a "force versus time" curve for the fourth embodiment of this invention.
Figure 22:
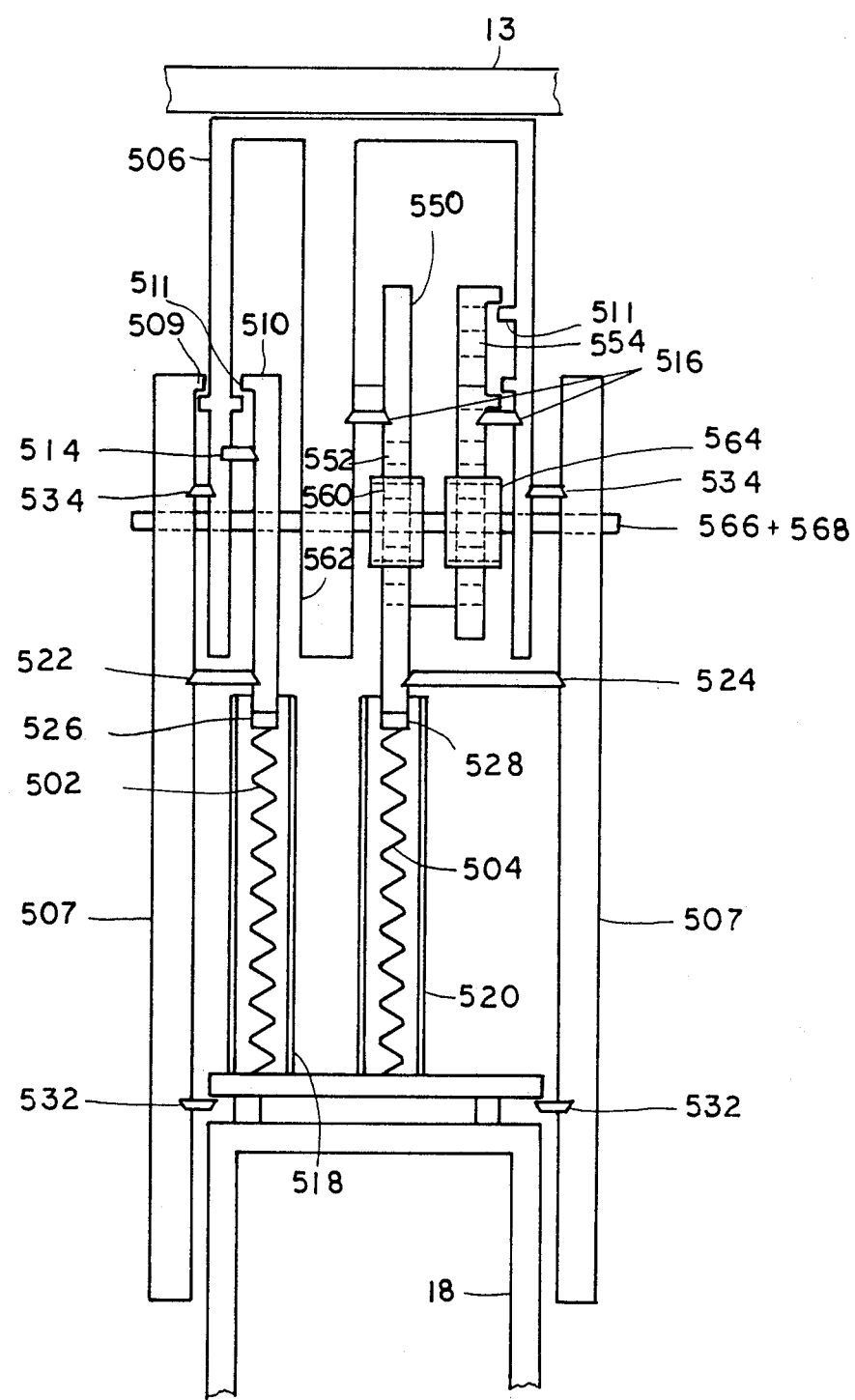
FIG. 22 is a side view of the fourth leg-brace embodiment of this invention, showing the location of the first sequenced storage means and the various racks and pinions used to reverse the compression of the second sequenced storage means.
Figures 23, 24:
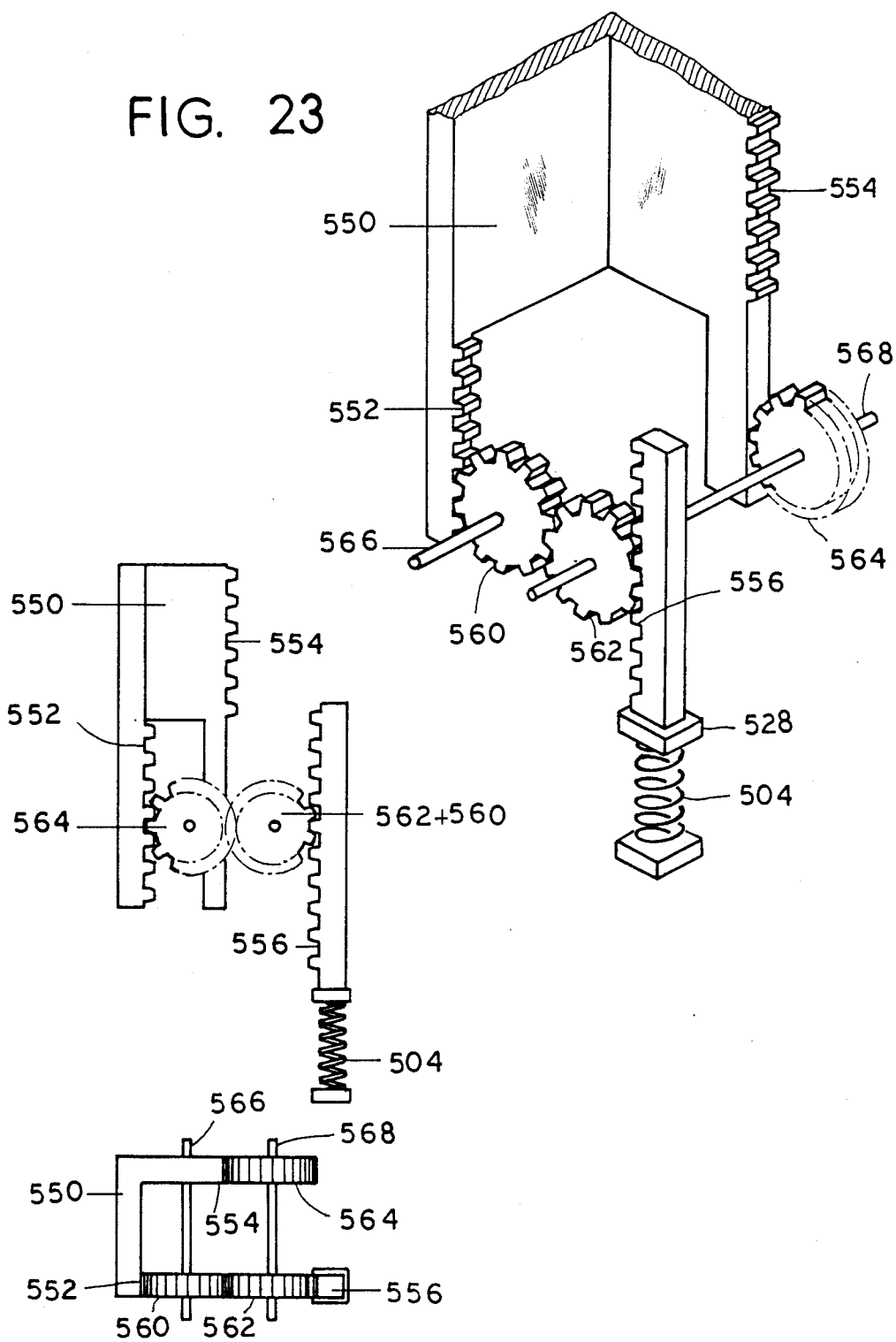
FIG. 23 is a perspective view of the fourth leg-brace embodiment of this invention, showing the location of the first sequenced storage means and the various racks and pinions used to reverse the compression of the second sequenced storage means.
FIG. 24 shows both a side and a top view of the fourth leg-brace embodiment of this invention, showing the location of the first sequenced storage means and the various racks and pinions used to reverse the compression of the second sequenced storage means.

The fourth leg-brace embodiment uses sequenced storage means as shown in FIGS. 21-24. The objective of this embodiment is to limit the impact force to a constant curve, as shown in the force-vs-time curve of FIG. 21, which does not return to zero in the sawtooth manner of the previous embodiment shown in FIG. 20. With reference to FIG. 22, this effect is achieved in a similar manner to that used in the previous leg-brace embodiment of FIG. 19, except that the second spring drive 512 of FIG. 21 is replaced with a reversing mechanism. Referring now to FIGS. 23 and 24, the reversing mechanism is comprised of double-rack drive 550 which has two racks facing the side direction, rack 552 opposite double gears 560 and 562 and rack 554 opposite single gear 564. The top of rack 552 is located at the same level as the bottom of rack 554. Axles 566 and 568 are anchored in outer brace 507, and slots in multiple channel housing 506 permit downward motion of this housing Rack spring drive 556 is moved vertically by gear 562.

Upon impact, multiple channel housing 506 moves downward, compressing storage means 502, as described above with reference to FIG. 19. Storage means 504 is compressed as follows: rack 552 engages gear 560 turning it counterclockwise, which turns gear 562 clockwise, which moves rack spring drive 556 downward, which compresses storage means 504. The total force compressing storage means 502 and 504 after they have traveled a distance $x_o/2$ equals the impact force $F_o$ of the runner's weight on the ground, as indicated by the initial ramp of slope $2k$ in FIG. 21. At this time, rack 552 ceases engaging gear 560, and, simultaneously, rack 554 commences engaging gear 564. The result is that storage means 504 pushes up rack 556 which turns gear 564 counterclockwise aiding the downward motion of double-rack drive 550 and opposing the action of storage means 502.

The sum action of these two forces, indicated by the slopes $+k$ and $-k$ in FIG. 21, yields a constant force $F_o$ acting to oppose the downward movement of multiple channel housing 506, and, hence, of pelvic harness 13. When storage means 502 and 504 are released, as described with respect to the previous leg-brace embodiment, the combined thrust begins as the sum of the expansion force $F_1$ of storage means 502 and the expansion force $F_2$ of storage means 504. Later, when storage means 504 expands to its neutral position, the downward slope becomes $-k$. Thus, the thrust force can be stronger than the impact force, resulting in better performance, within the limits of what can be safely borne by the leg.

The important point here is that a system of such pairs of storage means can be used to achieve optimal compliance, which is tantamount to the curve $F(x)=a$ constant. Ideally, the impact force curve should rise quickly to the maximum safe value and then remain constant until the impact force is absorbed.

Any desired shape of the $F(x)$ curve can be achieved either by replacing circular gears 562 and 564 with a system of conventional cam gears or by using more than one pair of storage means. The fact that any desired shape can be achieved means that optimized performance of a runner can be achieved.

To give more rationale to the leg-brace embodiment of FIGS. 20-24, it is desirable to have optimal compliance (give of the surface), optimal resilience (give back of the surface), and a minimum of foot-contact time. Unfortunately, these goals conflict, and the optimal trade-off must be found. The first problem is that optimal compliance (a lower curve) takes more time to absorb vertical momentum, prolonging the impact interval. This is a problem for two reasons: (1) it results in slower running, and (2) the muscles have to work against the ground longer, using more energy.

In the case of a single storage means, the shape of the curve in the impact interval is approximately the mirror reflection of that in the thrust interval. Thus, the thrust interval must be the same as the impact interval. The embodiments of FIGS. 20-24 improve upon this because the maximum force during the thrust interval is considerably greater than that during the impact interval. Another way to see this is to note that each interval is proportional to the inverse square root of the spring constant. During impact, the effective spring constant (the sum of the separate spring constants) is considerably less than it is when all the storage means release together during thrust. The result is that the penalty of greater foot-contact time, or equivalently, muscle-work time, need be paid only during the impact interval. Thus, the last two embodiments, which use sequential storage means, offer improved performance over the earlier embodiments which use single storage means.

In the sequential storage means embodiments of FIGS. 19-24 it may be necessary to restrict the value of the effective spring constant during thrust (equal to the sum of the sequenced spring constants) to a value that is not injurious to the foot and leg, especially the shins. In this case, the spring travel has to be correspondingly longer.

The previous four leg-brace embodiments provide means for energy to be stored in the leg-brace storage means as a result of foot impact force. The fifth leg-brace embodiment provides for energy to be stored in the leg-brace storage means during flight. In this embodiment, the work performed by any voluntary muscle group in the body can be used to provide such additional energy. For example, the runner can squeeze Sylphon bellows or pistons with his hands, arms or legs and the resulting force can be transmitted hydraulically by a tube to the storage/thrust mechanism. Alternatively, the runner can pull and push conventional piston or lever systems with the arms and legs, or the energy can be electrically stored and then transmitted to the storage mechanism by conventional electro-mechanical transducers.

This embodiment allows a more complete exercise because more muscles are involved, and this allows enhanced performance over what can be achieved when only the running muscles of the legs are used.

FIG. 25 shows the upper brace part, hereinafter referred to as the storage station, of the fifth leg-brace embodiment, and FIG. 26 shows the lower brace part, hereinafter referred to as the work station. In this embodiment the legs compress storage means 4 via hydraulic means. FIG. 25 shows Sylphon bellows 600 and 602 which are sandwiched between force plates 608 and 609, and 610 and 611, respectively. Force plates 609 and 611 are rigidly attached to outer brace 14, so that expansion of Sylphon bellows 600 and 602 causes plates 608 and 610 to move upward. Conventional ratchet/release means 612 and 614 transmit the upward force on force plates 608 and 610 to lower brace 18, which moves upward compressing storage means 4. Forks 616 and 618 are rigidly attached to force plates 609 and 611 at their upper end, and they merge to form the upper part of auxiliary brace 620 which extends downward to be rigidly attached to center force plate 632.

Referring now to FIG. 26, on either side of force plate 632 is a Sylphon bellows. Sylphon bellows 626 is compressed when foot and sole 1, rigidly attached to lower force plate 630, are lifted, thereby causing hydraulic fluid to flow up tube 604 and causing Sylphon bellows 600 (see FIG. 25) to expand and compress storage means 4. Upper force plate 634 moves vertically within guides 640. Downward motion of foot and sole 1 pulls cable 638 downward, thereby pulling upper force plate 634 downward and compressing Sylphon bellows 628. This forces hydraulic fluid up tube 606, which expands Sylphon bellows 602 and compresses storage means 4.

By varying the areas of Sylphon bellows 600 and 602 with respect to Sylphon bellows 626 and 628, a mechanical advantage is achieved. This ensures that the upward force exerted by the leg is sufficient to compress storage means 4, even when the foot has moved up and down several times during flight. Ratchet/release means 612 and 614 ensure that, once storage means 4 has been compressed, it cannot expand until thrust, at which time ratchet/release means 612 and 614 are released in the manner described above with respect to catch/release 16 of FIG. 1. Ratchet/release means 612 and 614 also ensure that, when either Sylphon bellows 626 or 628 expand, Sylphon bellows 600 or 602 contract with a minimum force, since lower brace 18 does not oppose downward motion of force plates 608 and 610.

Work done in flight by other muscle groups, such as the arms, can be stored in storage means 4 in a similar manner to that just described for the legs.

Figure 27:
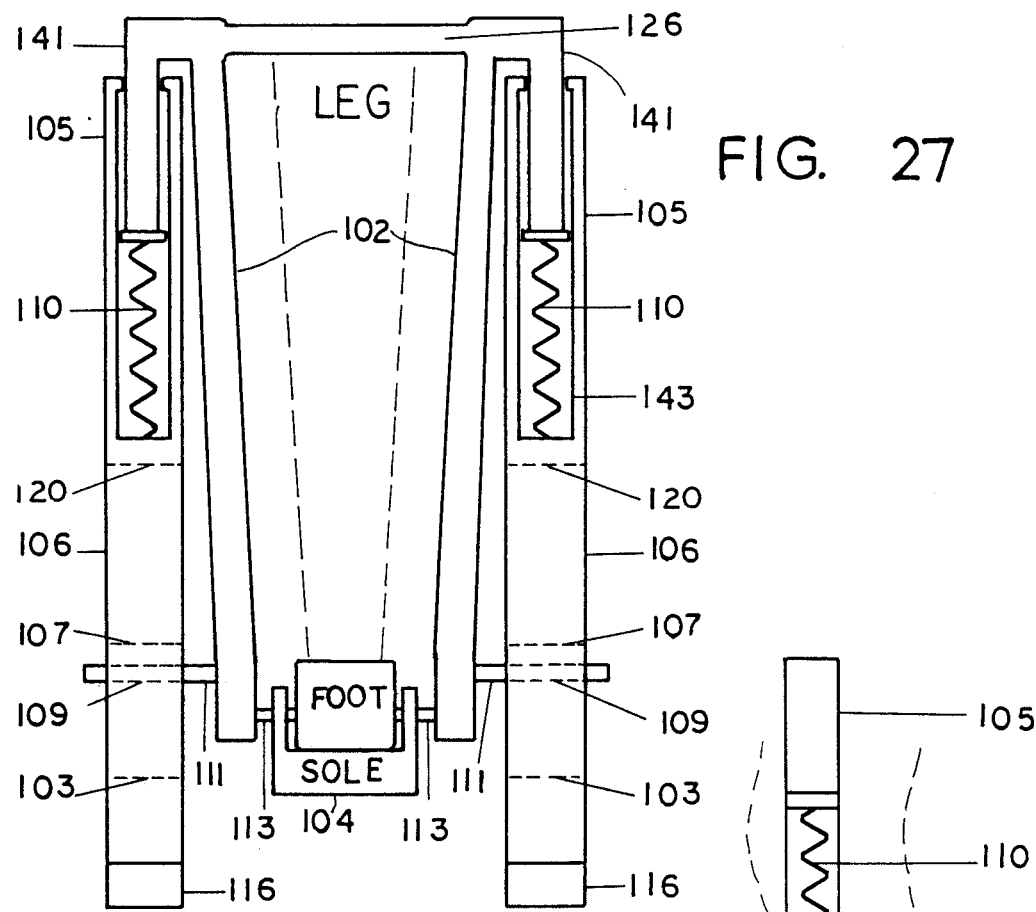
FIG. 27 is a front view of the sixth leg-brace embodiment of this invention, showing the location of the energy storage means when there is no pelvic harness.

FIG. 27 is a rear end-view of the sixth leg-brace embodiment. It does not require a hip harness and stores impact energy in a storage means located above a fork attached to the shoe sole. In this embodiment the storage means is located a sufficient distance above the sole so that it receives energy from the heel and then provides energy to the front of the sole, via the two fork legs.

The lower ends of a pair of inside supports 102 are rigidly attached to shoe sole 104, and the upper ends are rigidly attached to outside supports 105 by means of projections 141 which slide within channels 143 of supports 105. The bottoms of supports 105 contain rear forks 106, front forks 115 and fork rocker feet 116. The sole is suspended between supports 105 in such a manner that, upon impact, inside supports 102 compress storage means 110 against the top of forks 106. This cushions the force on the foot and, at the same time, stores the impact energy in storage means 110.

Guide bars 111 are rigidly attached to inner supports 102 on one side, and extend horizontally to the side, through vertical slots 109, which extend from positions 103 to 107. These guide bars constrain the forward motion of inner supports 102 with respect to outer supports 106.

Figure 28:
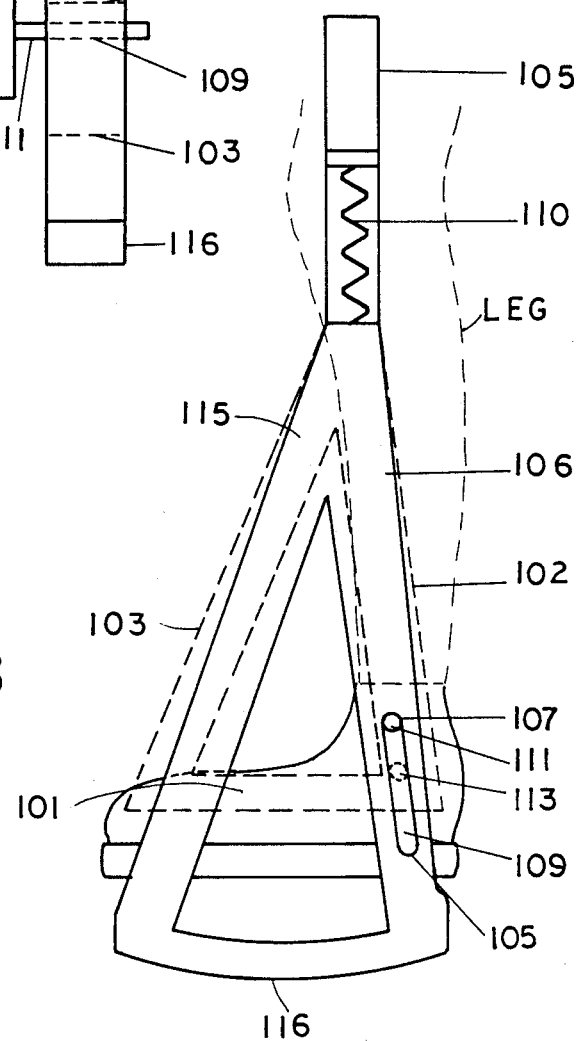
FIG. 28 is a side view of the sixth leg-brace embodiment of this invention, showing the location of the energy storage means when there is no pelvic harness.

FIG. 28 is a side view of outside support 105, showing outside rear fork 106 and outside front fork 115. At impact, rocker foot 116 strikes the ground first, compressing storage means 110 by inside brace 102, thereby storing the impact energy. While the runner's weight rolls over onto the front of rocker foot 116, the impact force is shared by rear and front forks 106 and 115, and then, during take off, storage means 110 expands, pushing against the ground through front fork 115. The lengths of outside support 105 and inside support 102, and the stiffness of storage means 110 are chosen so that the bottom of sole 104 just touches the ground at the end of impact. This allows the foot to provide adequate control and to contribute, along with the force exerted by storage means 110, to the take-off thrust without losing too much energy from the runner's foot impacting the ground directly.

Referring again to FIG. 27, the top of support 102 is fastened to conventional belt 126. This maintains close contact between inner support 102 and the leg, thereby providing for greater stability of the leg brace.

An important point that applies only to the sixth leg-brace embodiment is that storage means 110 acts in series with the leg rather in parallel, while in the other leg-brace embodiments the storage means acts in parallel with the leg. Thus, there is no direct increase in the effective spring constant, and there is no significant enhancement of performance in the this embodiment.

Figure 29:
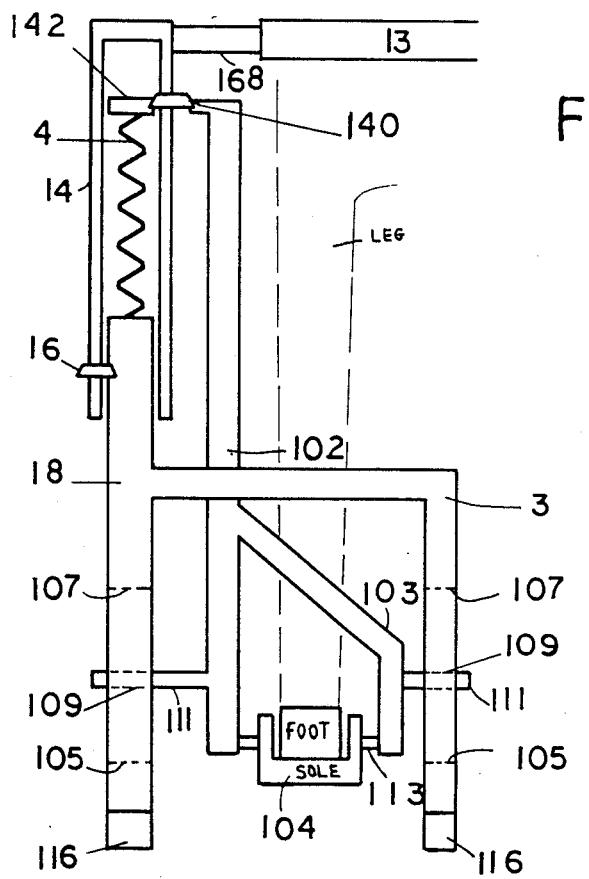
FIG. 29 is a front view of the seventh leg-brace embodiment of this invention, showing an alternative way to store impact energy borne by the runner's leg.

The seventh leg-brace embodiment of FIG. 29 is similar to the sixth leg-brace embodiment of FIG. 27, except that inner support 102 is engageable with upper spring plug 142 of FIG. 29 by ratchet/release means 140. During impact, the foot pushes down sole 104 which pulls down inner support 102 via axle 113, causing ratchet/release 140 to pull down upper spring plug 142 and compress storage means 4 from above. At the same time, rocker feet 116 impact the ground causing lower brace 18 to compress storage means 4 from below.

A proper delay in thrust by storage means 4 is achieved by ratchet/release means 16 as previously described in FIGS. 2 and 4 of the first leg-brace embodiment. During thrust, ratchet/release means 140 remains engaged, while ratchet/release means 16 releases, pushing against the ground and propelling the runner back into the air. After thrust, ratchet/release means 140 releases, allowing flexion of the runner's knees during flight to return ratchet/release means 140 and upper spring plug 142 to their original, pre-impact positions with respect to upper brace 14. Guide bars 111, vertical slots 109, and positions 105 and 107 have the same meanings described in the sixth leg-brace embodiment of FIG. 27. Swivel 168 is described in the next section for the pelvic harness of FIG. 30.

This seventh leg-brace embodiment, in effect, combines the first and sixth leg-brace embodiments, in that the storage means (4 in FIG. 2 and 110 in FIG. 25) corresponding to the first and sixth embodiments are one and the same in the seventh leg-brace embodiment. This ensures that the energy lost due to heel-sole impact in the first leg-brace embodiment is, instead, stored in storage means 4. Also, during initial impact before sole 104 contacts the ground, part of the impact force is transmitted to storage means 4 via the runner's leg, thereby relieving the load borne by pelvic harness 13. Thus, the seventh leg-brace embodiment accomplishes the same energy-efficiency goal as the second leg-brace embodiment, with the difference being that it does not use a separate storage means in the sole.

Harness

The purpose of the harness is to rigidly connect the upper parts of the runner's body to the various braces used in the invention. The leg brace serves to protect the legs from impact shock, but this is only possible if the upper mass is rigidly attached to the leg brace which then supports a portion of the impact force.

Figure 30:
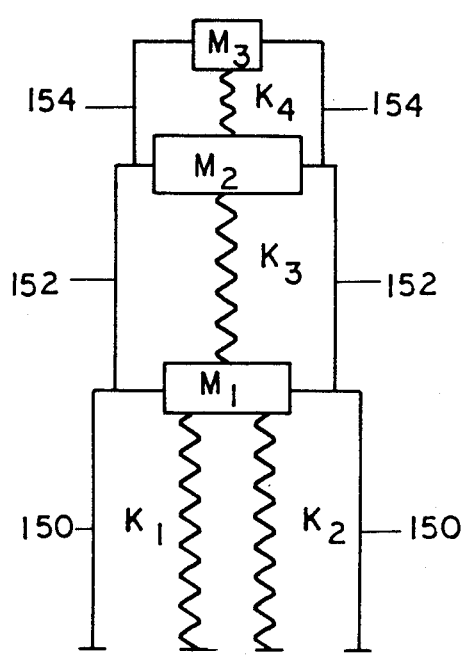
FIG. 30 is a schematic representation of the brace system of this invention.

FIG. 30 shows a model of the runner and the brace system. Mass $m_1$ represents the pelvic mass, $m_2$ the torso mass, and $m_3$ the head mass. Springs are indicated by their spring constants $k_i$. Thus, $k_1$ and $k_2$ represent the legs, $k_3$ the back, and $k_4$ the neck. The connective elements represented by the springs are the most susceptible to damage by impact shock. The purpose of the braces is to function as an exoskeleton to protect these connective elements from undue compression and impact shock. Thus, leg-brace pair 150 protects the legs, back-brace 152 the back, and neck-brace 154 the neck. Note that when the connective elements are protected, the new limit of tolerable impact shock is determined by the limits for the individual mass elements such as the head or the torso, and these limits are higher than those for the connective elements.

It is important, from the standpoint of optimum speed, to have rigid connections between the body masses and the braces to have a high effective spring constant of the entire mass-spring system. That is, there should be a minimum of "slop", or give, between the harnesses and the body, on the one hand, and the harnesses and the braces, on the other hand.

Figure 31:
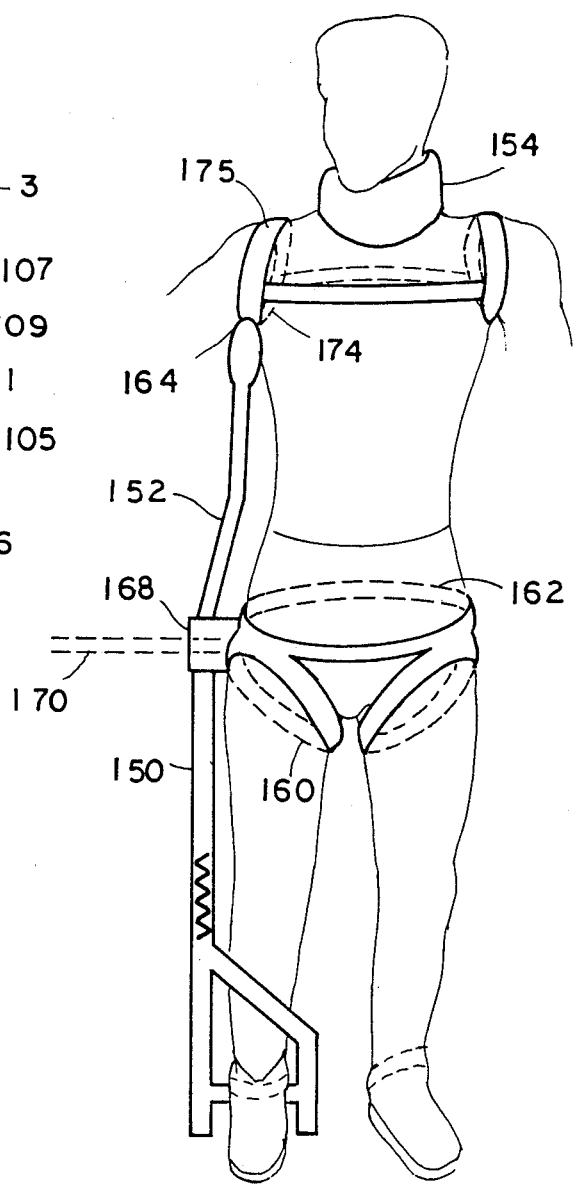
FIG. 31 is a front view of the harness and brace systems of this invention.

The best locations for harnesses are the pelvis, the shoulders, and the chin, and these will be discussed first. FIG. 31 shows a conventional pelvic harness which provides support under the legs 160 and around the seat at the pelvic level 162. The most important areas of support are 160 and 162 since these can support vertical weight without being uncomfortably tight.

Note that the brace and harnesses are located on both sides. Only one side will be described in the following description, since each side is identical. Leg brace 150 is rotatably attached to the pelvic harness at the sides by conventional swivel 168, in such a manner that said leg brace is free to rotate about imaginary axis 170 which is horizontal and which extends from side to side. Thus, the leg brace is free to follow the natural rotation of the legs about the same axis that occurs while running. Furthermore, leg brace 150 is attached to swivel 168 and then to the pelvic harness in such a manner that there is a minimum of vertical give between the top of the leg brace and the pelvis during impact.

Back brace 152 is rigidly attached to swivel 168 so that the impact shock is fully transmitted from leg brace 150, through swivel 168, up back brace 152, thereby protecting the runner's back. The top of said back-brace is rigidly attached to the shoulder harness at location 174.

The conventional shoulder harness passes under the armpits at 176 and around the chest and back. There is sufficient padding 164 under the armpits to prevent damage to the muscle elements in that area.

Conventional neck brace 154 rests on the runner's shoulders and supports the head at the chin and around the base of the skull, thereby protecting the neck from damage due to impact shock transmitted through the leg brace and then up the back brace.

Another embodiment of the body harness would utilize non-elastic pants or jacket, such as those used for scuba diving, except lighter and ventilated. These would distribute the impact load over a greater body area, and this would increase the rigidity of the harness.

The discussion regarding the invention has tacitly assumed a normal running gait in which the runner alternates from one foot to the other. Should research prove that it is possible to achieve a sufficiently high effective spring constant to bound sufficiently high into the air, then it may be possible for humans to run efficiently with a kangaroo gait. That is, the applications of the invention are not restricted to the normal gait. In this case, an additional lower brace in the back, simulating a kangaroo tail, would be helpful for front-to-back balance.

Other applications can be found in the areas of recreation, orthopedics, and robotic running.

Perhaps the most significant safety problem will be to protect the runner from falls from the great heights that may be achieved with this embodiment. The body brace could be constructed to function as a "basket roll-bar" to protect the runner. Similarly, it is entirely possible, in certain applications with relatively higher impact, that additional support members may be needed to ensure structural integrity of the brace system.

The above description shall not be construed as limiting the ways in which this invention may be practiced but shall be inclusive of many other variations that do not depart from the broad interest and intent of the invention.

Having thus described the invention, what is claimed as new and desired to be secured by Letters Patent is:

1. In an energy-efficient running brace comprising brace means for supporting and protecting a runner's legs during impact on a running surface and for storing the impact energy for release during thrust, and harness means for attaching the runner's body to said brace means, the improvement comprising auxiliary transmission means for transmitting during flight to said brace means energy generated by movement of the runner's limbs other than foot impact energy, and for releasing said non-foot-impact energy during take-off from said running surface and storage means connected to said brace means for storing said non-foot-impact energy during flight.

2. The improved energy-efficient running brace of claim 1, wherein said brace means comprises:
    an upper brace rotatably connected to said harness means; and
    a lower brace coupled to said storage means for compressing said storage means and for transmitting said non-foot impact energy from said running surface to said storage means during take-off.

3. The improved energy-efficient running brace of claim 2, wherein said auxiliary transmission means comprises:
    a storage station proximate to said storage means for using said non-foot-impact energy to compress said storage means; and
    a work station proximate to said limbs for allowing said limbs to work against said storage means by transmitting said limb force to said storage station.

4. The improved energy-efficient running brace of claim 3, wherein said storage station comprises a first energy storage means and a second energy storage mans, each of which comprises:
    a hydraulic transmission mechanism attached to said upper brace;
    a bottom plate rigidly attached to the bottom of said hydraulic transmission mechanism and to said upper brace;
    a ratchet plate rigidly attached to the top of said hydraulic transmission mechanism wherein said ratchet plate moves said lower brace upward, thereby compressing said storage means during flight; and
    storage station ratchet/release means attached to said lower brace through a slot in said upper brace and attached to said ratchet plate for allowing said storage means to expand at the beginning of take-off from said running surface.

5. The improved energy-efficient running brace of claim 3, wherein such storage station comprises a first energy storage means and a second energy storage means and where said work station comprises:
    a center plate rigidly attached to said lower brace in the vicinity of said limbs;
    an upper hydraulic transmission mechanism located above said center plate and rigidly attached thereto;
    a lower hydraulic transmission mechanism located below said center plate and rigidly attached thereto;
    a top bellows plate rigidly attached to the top of said upper hydraulic transmission mechanism;
    a bottom bellows plate rigidly attached to the bottom of said lower hydraulic transmission mechanism;
    an upper hydraulic tube connecting said upper hydraulic transmission mechanism to said storage station;

a lower hydraulic tube connecting said lower hydraulic transmission mechanism to said storage station;
means for rigidly attaching said bottom bellows plate to one of said limbs; and
a cable attaching said top bellows plate to said limb, wherein movement of said limb in one direction compresses said lower hydraulic transmission mechanism between said bottom bellows plate and said center plate, causing hydraulic fluid to flow through said lower hydraulic tube to said storage station and causing compression of said first energy storage means, and wherein movement of said limb in the opposite direction compresses said upper hydraulic transmission mechanism between said top bellows plate and said center plate, causing hydraulic fluid to flow through said upper hydraulic tube and causing compression of said second energy storage means.

* * * * *